(12) United States Patent
Piccinelli et al.

(10) Patent No.: US 7,498,293 B2
(45) Date of Patent: Mar. 3, 2009

(54) ALKYLAMINOSILOXANES AS CORROSION INHIBITORS

(75) Inventors: Piero Piccinelli, Sasso Marconi (IT); Stefano Gardi, Bologna (IT); Giovanni Da Roit, Sasso Marconi (IT)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 707 days.

(21) Appl. No.: 10/516,128

(22) PCT Filed: May 22, 2003

(86) PCT No.: PCT/EP03/05372

§ 371 (c)(1),
(2), (4) Date: Nov. 29, 2004

(87) PCT Pub. No.: WO03/101947

PCT Pub. Date: Dec. 11, 2003

(65) Prior Publication Data

US 2005/0176596 A1    Aug. 11, 2005

(30) Foreign Application Priority Data

May 31, 2002    (EP)    .................. 02405441

(51) Int. Cl.
*C07F 7/10* (2006.01)
*C07F 7/08* (2006.01)
*C10M 169/04* (2006.01)

(52) U.S. Cl. ...................... 508/207; 508/202

(58) Field of Classification Search ................ 508/202, 508/207
See application file for complete search history.

(56) References Cited

U.S. PATENT DOCUMENTS

| | | | |
|---|---|---|---|
| 3,524,900 A * | 8/1970 | Gibbon et al. ............. 525/478 |
| 3,814,710 A * | 6/1974 | Duncan ..................... 106/10 |
| 3,941,856 A * | 3/1976 | Creasey et al. ............. 525/478 |
| 4,131,583 A | 12/1978 | Boerwinkle ................ 260/29.6 |
| 4,275,835 A | 6/1981 | Miksic et al. ................. 239/60 |
| 4,406,807 A | 9/1983 | Renner et al. .............. 252/78.3 |
| 4,973,448 A | 11/1990 | Carlson et al. ................ 422/9 |
| 5,246,607 A | 9/1993 | Schaefer et al. ........ 252/389.32 |
| 5,393,457 A | 2/1995 | Miksic et al. ............... 252/194 |
| 5,463,058 A * | 10/1995 | Carrozza et al. ............. 546/14 |
| 5,879,436 A * | 3/1999 | Kramer et al. ........... 106/14.42 |
| 5,937,618 A | 8/1999 | Chandler ..................... 53/427 |
| 6,033,599 A | 3/2000 | Lozano et al. ......... 252/389.54 |
| 2002/0031729 A1 * | 3/2002 | Trefonas et al. ............. 430/322 |

FOREIGN PATENT DOCUMENTS

| | | |
|---|---|---|
| DE | 2254117 | 5/1974 |
| EP | 0368119 | 5/1990 |
| GB | 1458533 | 12/1976 |
| WO | 97/01606 | 1/1997 |
| WO | 02/33146 | 4/2002 |

OTHER PUBLICATIONS

Patterson, W.J., and Bilow, N., J. Polymer Sci., 1969, 7, 1089-1110.*
M. Alagar et al., British Corrosion Journal, vol. 34, No. 1, (1999) pp. 76-78.
Derwent Abstract 1987-255336 [36] for SU 1283512 (1987).

* cited by examiner

*Primary Examiner*—Glenn Caldarola
*Assistant Examiner*—Jim Goloboy
(74) *Attorney, Agent, or Firm*—Tyler A. Stevenson

(57) ABSTRACT

The instant invention discloses a composition comprising a carrier, preferably a packaging material, and at least one compound of the formula (I) in which the general symbols are as defined in claim 1 as corrosion inhibor for protecting metallic surfaces.

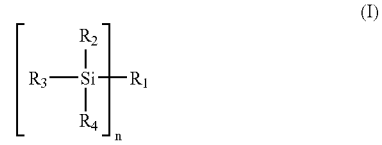

16 Claims, No Drawings

ALKYLAMINOSILOXANES AS CORROSION INHIBITORS

The present invention relates to compositions comprising a carrier, preferably a packaging material, and alkylaminosiloxanes as corrosion inhibitors, to the use thereof in compositions for protecting metallic surfaces and to novel alkylaminosiloxanes.

Corrodible materials, for example iron or steel, are subjected to a variety of corrosive environments between the time when they are manufactured and the time when they actually are used in the manufacture of an intended product. Newly manufactured metallic articles frequently have fresh metal surfaces which are highly susceptible to corrosion. Corrosive environments for the metals during for example shipment, storage or handling are for example air, air containing high humidity, corrosive gasses and rain or surface condensation.

Plastic packaging processes are widely used in the packaging of articles. While conventional packaging applications provide protection of the article for mechanical purposes prior to sale to the ultimate consumer, these types of packaging may require additional protection to inhibit potential damage from humid and/or corrosive environments. For example, the permeability of plastic packaging permits the introduction of water vapors and other potentially harmful gaseous components into the package envelope. These corrosive components may be introduced into the envelope during extended shipping and storage times typically encountered between the completion of the packaging operation and the final transfer of the product to the ultimate consumer. Humid environments are almost universally encountered with varying degrees of severity. Fluctuations in temperature can cause condensation of the trapped water vapor and ultimate deposition of the condensate on metallic surfaces, which generates corrosion. Consequently, it is usually necessary to remove the undesirable corrosion, which is present on the surface of the material before the purchaser may satisfactorily use such material. This may be a very expensive and time-consuming process. Additionally, when the metal material is used in the manufacture of such products as painted or electroplated articles, even small amounts of corrosion of the metal render such metal completely unsatisfactory for its intended purpose.

In attempts to reduce or eliminate corrosion of metal during shipment and storage, various types of coatings and temporary protectants have been proposed. For example, it is possible to simply coat the metal with an oil, grease or wax. However, such types of coatings are not always effective, and they may be quite undesirable due to their flammability or oily nature. Furthermore, such types of coatings normally must be completely removed from the metal surface before the metal may be used in many manufacturing processes. Such a removal naturally is time consuming and also requires the use of solvents, with attendant expense and pollution problems. Although the addition of conventional corrosion inhibiting materials to such oils, greases and waxes may render such types of coatings more effective, the problems associated with removal of the coating, when necessary, are not alleviated.

Solid corrosion inhibitors, present a different set of disadvantages. Particulate materials can foul certain mechanical items and can be difficult to remove from the protected items when finally unpacked or otherwise put to use. In other applications, solid phase or liquid phase compounds are used which are generally referred to as volatile corrosion inhibitors (VCI). Such compounds vaporize and form a relatively stable bond at the air/metal interface thus producing a very thin layer that inhibits the electrochemical corrosion reaction. Because molecules in the vapor phase disperse very rapidly, even at ambient conditions or even cooler temperatures, a vapor phase corrosion inhibitor will generally set up an equilibrium environment rather quickly. In such an environment, the corrosion inhibiting compounds can reach and protect all of the items in the enclosed environment, even in the most recessed areas and cavities of the metal, much more efficiently than could solids or liquids, which are only effective when in contact with the corrodible substrate. Additionally, because of their rapid dispersal, removal of the protective emitted vapors from the items is unnecessary when the items themselves are removed from their respective packages. Several techniques for using volatile corrosion inhibitors have evolved to date. One method comprises forming a tablet or some other solid shaped element from a solid compound, which will release, the vapor phase corrosion inhibitor. In other techniques package walls or other substrates are painted or coated with volatile corrosion inhibitor-containing compositions, which release protective vapors. Other techniques blend volatile corrosion inhibitor compounds with or impregnate them into materials such as foamed compositions so that a foamed article protects the items from physical shock, as well as from corrosion. Another method comprises the blending of volatile corrosion inhibitors with a polymer powder which is extruded at high temperature to packaging articles which contain the corrosion inhibitors. Some of the liquid or solid corrosion inhibiting compounds used in such techniques include volatile molecules like for example triazoles; organic or inorganic nitrites, nitrates, chromates, molybdates, carbonates, carboxylates, phosphates; primary, secondary, tertiary or quaternary amines (aliphatic or aromatic) or their organic or inorganic acid salts. Typical vapor phase inhibitors are for example isopropylamine, cyclohexylamine, benzylamine, allylamine, diethyl or diisopropylamine, dicyclohexylamine, piperidine, triisopropylamine, aminoalchols, dicyclohexyammonium nitrite, diisopropylammonium nitrite, dicyclohexylammonium nitrophenate, cyclohexylammonium nitrophenate, cyclohexylamine chromate, cyclohexylamine m-mononitro-benzoate, dicyclohexylamine chromate, cyclohexylamine benzoate, monoethanolamine benzoate, diethanolamine benzoate or mixtures thereof. Examples of such references are U.S. Pat. Nos. 4,131,583; 4,275,835; 4,973,448; 5,393,457; 5,937,618 or U.S. 6,033,599.

The compounds with corrosion inhibiting properties must have a sufficient volatility in order to act in the vapor phase at room temperature. However, a high volatility is a disadvantage when these compounds are incorporated into organic polymeric materials at high temperatures. Additionally, these compounds must have a high thermal stability. A lower processing temperature is often not possible because of the physicochemical properties of the organic polymeric material and the drastically reduction of the economical output.

These known volatile corrosion inhibitors do not satisfy in every respect the high requirements which a corrosion inhibitor is required to meet, especially with regard to incorporation into plastics at high temperature, generating undesired fume or bad odor.

It has now been found that a selected group of alkylaminosiloxanes is particularly suitable for use as corrosion inhibitors for protecting metallic surfaces.

The present invention therefore provides a composition comprising
  a) a carrier, and
  b) as corrosion inhibitor at least one compound of the formula I

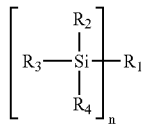
(I)

wherein, when n is 1,
R₁ is hydrogen, $C_1$-$C_{32}$alkyl, $C_2$-$C_{32}$alkenyl, $C_2$-$C_{32}$alkynyl, unsubstituted or $C_1$-$C_4$alkyl-substituted phenyl; $C_7$-$C_9$phenylalkyl, $C_1$-$C_{32}$alkoxy, $C_2$-$C_{32}$alkenyloxy, $C_2$-$C_{32}$alkynyloxy, unsubstituted or $C_1$-$C_4$alkyl-substituted $C_5$-$C_8$cycloalkyl; unsubstituted or $C_1$-$C_4$-alkyl-substituted $C_5$-$C_8$cycloalkoxy;

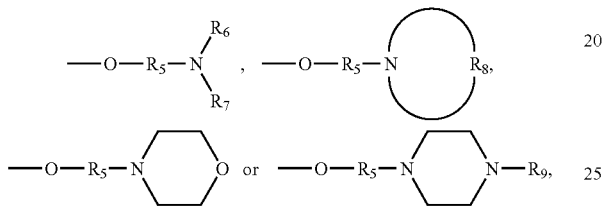

when n is 2,
R₁ is $C_1$-$C_{32}$alkylene, $C_2$-$C_{32}$alkylene interrupted by oxygen; $C_5$-$C_8$cycloalkylene or —R₁₀—O—R₁₂—O—R₁₁—,
when n is 3,
R₁ is $C_1$-$C_{32}$alkanetriyl,

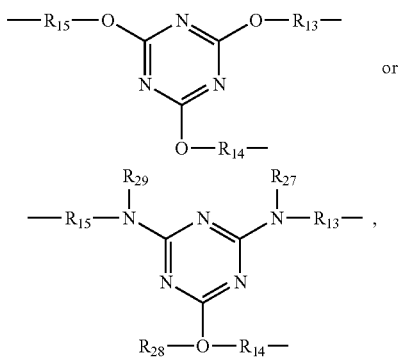

or when n is 4,
R₁ is $C_1$-$C_{32}$alkanetetrayl,

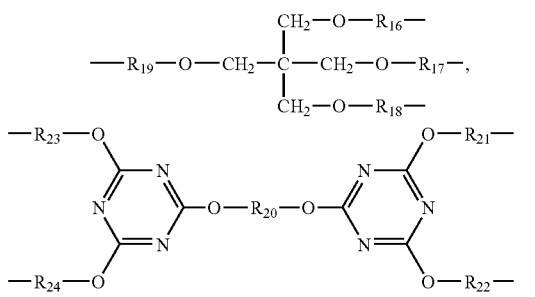

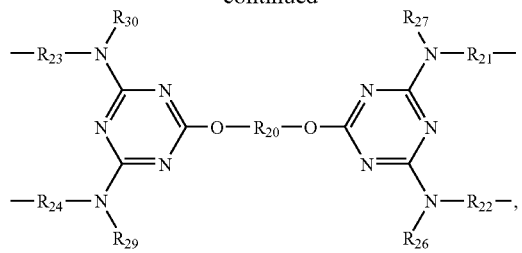

R₂, R₃ and R₄ are each independently of the others $C_1$-$C_{32}$alkyl, $C_2$-$C_{32}$alkenyl, $C_2$-$C_{32}$alkynyl, unsubstituted or $C_1$-$C_4$alkyl-substituted phenyl; $C_7$-$C_9$phenylalkyl, $C_7$-$C_9$phenylalkoxy, $C_1$-$C_{32}$alkoxy, $C_2$-$C_{32}$alkenyloxy, $C_2$-$C_{32}$alkynyloxy, unsubstituted or $C_1$-$C_4$-alkyl-substituted $C_5$-$C_8$cycloalkyl; unsubstituted or $C_1$-$C_4$alkyl-substituted $C_5$-$C_8$cycloalkoxy;

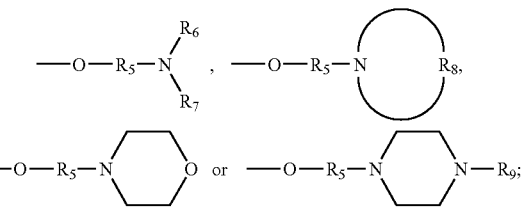

with the proviso that at least one of the radicals R₂, R₃ or R₄ is $C_2$-$C_{32}$alkynyloxy,

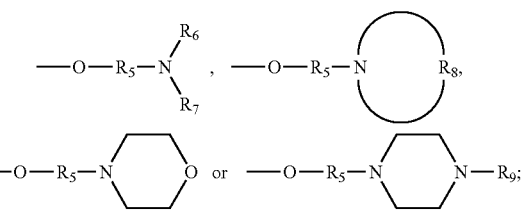

R₅ is $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene,
R₆ and R₇ are each independently of one another hydrogen or $C_1$-$C_{12}$alkyl,
R₈ is unsubstituted or $C_1$-$C_4$alkyl-substituted $C_2$-$C_{12}$alkylene;
R₉ is $C_1$-$C_{25}$alkyl, $C_2$-$C_{25}$alkyl interrupted by oxygen; $C_7$-$C_9$phenylalkyl, unsubstituted or $C_1$-$C_4$alkyl-substituted $C_5$-$C_8$cycloalkyl; unsubstituted or $C_1$-$C_4$alkyl-substituted phenyl;
R₁₀ and R₁₁ are each independently of one another $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene;
R₁₂ is $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$Cycloalkylene, unsubstituted or $C_1$-$C_4$alkyl-substituted phenylene; unsubstituted or $C_1$-$C_4$alkyl-substituted naphthylene; or

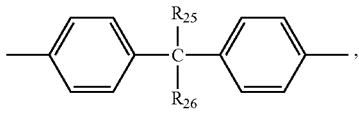

$R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are each independently of the others $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene;

$R_{25}$ and $R_{26}$ are each independently of one another hydrogen, $CF_3$, $C_1$-$C_{12}$alkyl or phenyl, or $R_{25}$ and $R_{26}$ together with the linking carbon atom, form a $C_5$-$C_8$cycloalkylidene ring which is unsubstituted or substituted by 1 to 3 $C_1$-$C_4$alkyl groups;

$R_{27}$, $R_{28}$, $R_{29}$ and $R_{30}$ are each independently of the others hydrogen or $C_1$-$C_8$alkyl; and n is 1, 2, 3 or 4.

Alkyl having up to 32 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, icosyl or docosyl.

Alkenyl having 2 to 32 carbon atoms is a branched or unbranched radical such as, for example, vinyl, propenyl, 2-butenyl, 3-butenyl, isobutenyl, n-2,4-pentadienyl, 3-methyl-2-butenyl, n-2-octenyl, n-2-dodecenyl, iso-dodecenyl, oleyl, n-2-octadecenyl or n-4-octadecenyl. Preference is given to alkenyl having 2 to 18, especially 3 to 12, for example 3 to 6, especially 3 to 4 carbon atoms.

Alkynyl having 2 to 32 carbon atoms is a branched or unbranched radical such as, for example, —C≡CH, propynyl (propargyl), 2-butynyl, 3-butynyl, isobutynyl, n-2,4-pentadiynyl, 3-methyl-2-butynyl, n-2-octynyl, n-2-dodecynyl, iso-dodecynyl, n-2-octadecynyl or n-4-octadecynyl. Preference is given to alkynyl having 3 to 18, especially 3 to 12, for example 3 to 6, especially 3 to 4 carbon atoms.

$C_1$-$C_4$Alkyl-substituted phenyl, which contains preferably from 1 to 3, especially 1 or 2, alkyl groups, is, for example, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

$C_7$-$C_9$Phenylalkyl is, for example, benzyl, α-methylbenzyl, α,α-dimethylbenzyl or 2-phenylethyl. Preference is given to benzyl.

Alkoxy having up to 32 carbon atoms is a branched or unbranched radical, for example methoxy, ethoxy, propoxy, isopropoxy, n-butoxy, isobutoxy, pentyloxy, isopentyloxy, hexyloxy, heptyloxy, octyloxy, decyloxy, undecyloxy, dodecyloxy, hexadecyloxy or octadecyloxy.

Alkenyloxy of 2 to 32 carbon atoms is a branched or unbranched radical, for example vinyloxy, propenyloxy, 2-butenyloxy, 3-butenyloxy, isobutenyloxy, n-2,4-pentadienyloxy, 3-methyl-2-butenyloxy, n-2-octenyloxy, n-2-dodecenyloxy, isododecenyloxy, oleyloxy, n-2-octadecenyloxy or n-4-octadecenyloxy. It is preferred to use alkenyloxy of 3 to 12, in particular of 3 to 6, most preferably of 3 to 4, carbon atoms.

Alkynyloxy having 2 to 32 carbon atoms is a branched or unbranched radical such as, for example, vinyloxy, propynyloxy, 2-butynyloxy, 3-butynyloxy, isobutynyloxy, n-2,4-pentadiynyloxy, 3-methyl-2-butynyloxy, n-2-octynyloxy, n-2-dodecynyloxy, iso-dodecynyloy, n-2-octadecynyloxy or n-4-octadecynyloxy. Preference is given to alkynyloxy having 3 to 18, especially 3 to 12, for example 3 to 6, especially 3 to 4 carbon atoms.

Unsubstituted or $C_1$-$C_4$alkyl-substituted $C_5$-$C_8$cycloalkyl is, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Preference is given to cyclohexyl.

Unsubstituted or $C_1$-$C_4$alkyl-substituted $C_5$-$C_8$cycloalkoxy is, for example, cyclopentoxy, methylcyclopentoxy, dimethylcyclopentoxy, cyclohexyloxy, methylcyclohexyloxy, dimethylcyclohexyloxy, trimethylcyclohexyloxy, tert-butylcyclohexyloxy, cycloheptyloxy or cyclooctyloxy. Preference is given to cyclohexyloxy.

$C_1$-$C_{32}$Alkylene is a branched or unbranched radical, for example methylene, ethylene, propylene, tetramethylene, pentamethylene, hexamethylene, heptamethylene, octamethylene, decamethylene, dodecamethylene or octadecamethylene.

$C_2$-$C_{32}$Alkylene which is interrupted by oxygen is, for example, —CH$_2$—O—CH$_2$—, —CH$_2$—O—CH$_2$CH$_2$—, —CH$_2$CH$_2$—O—CH$_2$CH$_2$—, —CH$_2$CH$_2$—O—CH$_2$CH$_2$—O—CH$_2$CH$_2$—, —CH$_2$CH$_2$—(O—CH$_2$CH$_2$—)$_2$O—CH$_2$CH$_2$—, —CH$_2$CH$_2$—(O—CH$_2$CH$_2$—)$_3$O—CH$_2$CH$_2$— or —CH$_2$CH$_2$—(O—CH$_2$CH$_2$—)$_4$O—CH$_2$CH$_2$—.

$C_5$-$C_8$Cycloalkylene is a saturated hydrocarbon group having two free valences and at least one ring unit and is, for example, cyclopentylene, cyclohexylene, cycloheptylene or cyclooctylene. Preference is given to cyclohexylene.

$C_1$-$C_{32}$Alkanetriyl is for example

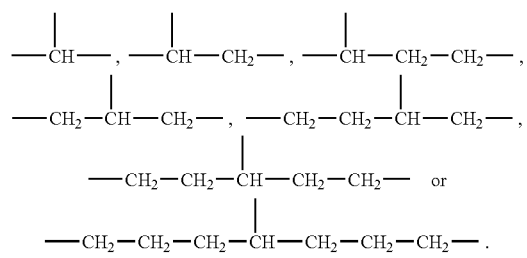

$C_1$-$C_{32}$Alkanetetrayl is for example

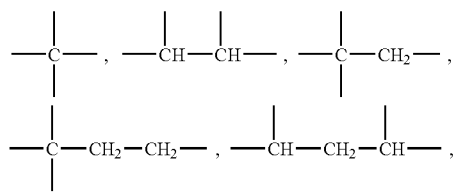

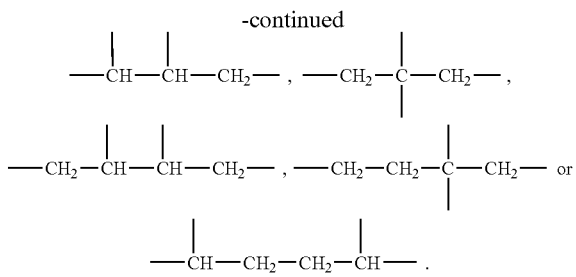

C$_7$-C$_9$Phenylalkoxy is, for example, benzyloxy, α-methylbenzyloxy, α,α-dimethylbenzyloxy or 2-phenylethoxy. Preference is given to benzyloxy.

C$_2$-C$_{18}$Alkenylene is a branched or unbranched radical such as, for example, vinylene, propenylene, 2-butenylene, 3-butenylene, isobutenylene, n-2,4-pentadienylene, 3-methyl-2-butenylene, n-2-octenylene, n-2-dodecenylene, isododecenylene, oleylene, n-2-octadecenylene or n-4-octadecenylene. Preference is given to alkenyl 3 to 12, for example 3 to 6, especially 3 to 4 carbon atoms.

Alkylidene having from 2 to 20 carbon atoms is, for example, ethylidene, propylidene, butylidene, pentylidene, 4-methylpentylidene, heptylidene, nonylidene, tridecylidene, nonadecylidene, 1-methylethylidene, 1-ethylpropylidene or 1-ethylpentylidene. Preference is given to C$_2$-C$_8$alkylidene.

Phenylalkylidene having from 7 to 20 carbon atoms is, for example, benzylidene, 2-phenyl-ethylidene or 1-phenyl-2-hexylidene. Preference is given to C$_7$-C$_9$phenylalkylidene.

Phenylene or naphthylene each unsubstituted or substituted by C$_1$-C$_4$alkyl is, for example, 1,2-, 1,3- or 1,4-phenylene; 1,2-, 1,3-, 1,4-, 1,6-, 1,7-, 2,6- or 2,7-naphthylene.

Unsubstituted or C$_1$-C$_4$alkyl-substituted C$_2$-C$_{12}$alkylene is a branched or unbranched radical, for example methylene, ethylene, propylene, 2-methylpropylene, tetramethylene, 2,2-di-methylbutylene, pentamethylene, hexamethylene, heptamethylene, octamethylene, decamethylene, dodecamethylene or octadecamethylene.

C$_2$-C$_{25}$Alkyl which is interrupted by oxygen is, for example, CH$_3$—O—CH$_2$—, CH$_3$—O—CH$_2$CH$_2$—, CH$_3$CH$_2$—O—CH$_2$CH$_2$—, CH$_3$CH$_2$—O—CH$_2$CH$_2$—O—CH$_2$CH$_2$—, CH$_3$CH$_2$—(O—CH$_2$CH$_2$—)$_2$O—CH$_2$CH$_2$—, CH$_3$CH$_2$—(O—CH$_2$CH$_2$—)$_3$O—CH$_2$CH$_2$— or CH$_3$CH$_2$—(O—CH$_2$CH$_2$—)$_4$O—CH$_2$CH$_2$—.

A C$_5$-C$_8$cycloalkylidene ring which is unsubstituted or substituted by 1 to 3 C$_1$-C$_4$alkyl groups, which contains preferably 1 or 2 branched or unbranched alkyl groups, is, for example, cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cycloheptylidene or cyclooctylidene. Preference is given to cyclohexylidene.

Preferred compositions comprise compounds of the formula I, wherein, when n is 1, R$_1$ is hydrogen, C$_1$-C$_{32}$alkyl, C$_2$-C$_{32}$alkenyl, C$_3$-C$_{32}$alkynyl, unsubstituted or C$_1$-C$_4$alkyl-substituted phenyl; C$_7$-C$_9$phenylalkyl, C$_1$-C$_{32}$alkoxy, C$_2$-C$_{32}$alkenyloxy, C$_2$-C$_{32}$alkynyloxy, unsubstituted or C$_1$-C$_4$alkyl-substituted C$_5$-C$_8$cycloalkyl; unsubstituted or C$_1$-C$_4$alkyl-substituted C$_5$-C$_8$cycloalkoxy;

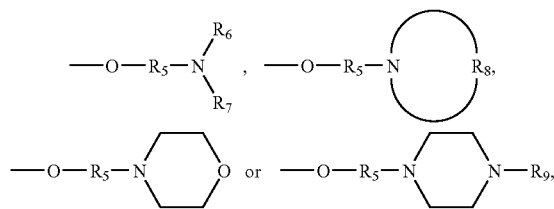

when n is 2,
R$_1$ is C$_1$-C$_{32}$alkylene, C$_2$-C$_{18}$alkylene interrupted by oxygen; C$_5$-C$_8$cycloalkylene or —R$_{10}$—O—R$_{12}$—O—R$_{11}$—,
when n is 3,
R$_1$ is C$_1$-C$_{32}$alkanetriyl,

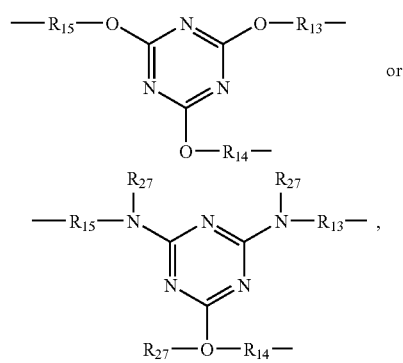

when n is 4,
R$_1$ is C$_1$-C$_{32}$alkanetetrayl

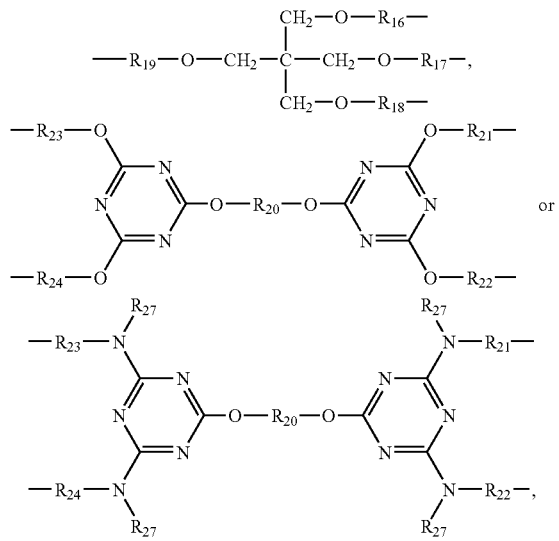

R$_2$, R$_3$ and R$_4$ are each independently of the others C$_1$-C$_{32}$alkyl, C$_2$-C$_{32}$alkenyl, C$_3$-C$_{32}$alkynyl, unsubstituted or C$_1$-C$_4$alkyl-substituted phenyl; C$_7$-C$_9$phenylalkyl, C$_7$-C$_9$phenylalkoxy, C$_1$-C$_{32}$-alkoxy, C$_2$-C$_{32}$alkenyloxy, C$_2$-C$_{32}$alkynyloxy, unsubstituted or C$_1$-C$_4$alkyl-substituted C$_5$-C$_8$-cycloalkyl; unsubstituted or C$_1$-C$_4$alkyl-substituted C$_5$-C$_8$cycloalkoxy;

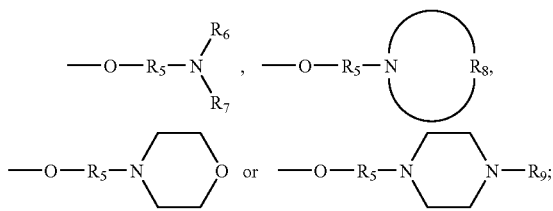

with the proviso that at least one of the radicals $R_2$, $R_3$ or $R_4$ is $C_2$-$C_{32}$alkynyloxy,

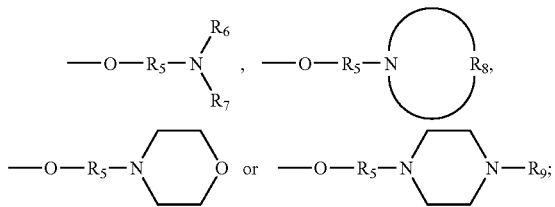

$R_5$ is $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene, $R_6$ and $R_7$ are each independently of one another hydrogen or $C_1$-$C_{12}$alkyl, $R_8$ is unsubstituted or $C_1$-$C_4$alkyl-substituted $C_2$-$C_{12}$alkylene;

$R_9$ is $C_1$-$C_{25}$alkyl, $C_2$-$C_{25}$alkyl interrupted by oxygen; $C_7$-$C_9$phenylalkyl, unsubstituted or $C_1$-$C_4$alkyl-substituted $C_5$-$C_8$cycloalkyl; unsubstituted or $C_1$-$C_4$alkyl-substituted phenyl;

$R_{10}$ and $R_{11}$ are each independently of one another $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene;

$R_{12}$ is $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene; unsubstituted or $C_1$-$C_4$alkyl-substituted naphthylene; or

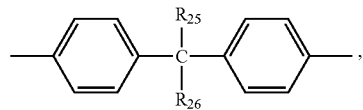

$R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are each independently of the others $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene;

$R_{25}$ and $R_{26}$ are each independently of one another hydrogen, $CF_3$, $C_1$-$C_{12}$alkyl or phenyl, or $R_{25}$ and $R_{26}$ together with the linking carbon atom, form a $C_5$-$C_8$cycloalkylidene ring which is unsubstituted or substituted by 1 to 3 $C_1$-$C_4$alkyl groups;

$R_{27}$ is hydrogen or $C_1$-$C_8$alkyl; and n is 1, 2, 3 or 4.

Interesting compositions are those comprising compounds of formula I wherein, when n is 1, $R_1$ is hydrogen, $C_1$-$C_{18}$alkyl, $C_2$-$C_{18}$alkenyl, $C_3$-$C_{18}$alkynyl, unsubstituted or $C_1$-$C_4$alkyl-substituted phenyl; $C_7$-$C_9$phenylalkyl, $C_1$-$C_{10}$alkoxy, $C_2$-$C_{18}$alkenyloxy, $C_2$-$C_{18}$alkynyloxy, unsubstituted or $C_1$-$C_4$alkyl-substituted $C_5$-$C_8$cycloalkyl; unsubstituted or $C_1$-$C_4$alkyl-substituted $C_5$-$C_8$cycloalkoxy;

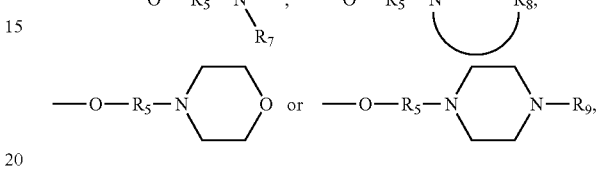

when n is 2, $R_1$ is $C_1$-$C_{18}$alkylene, $C_4$-$C_{18}$alkylene interrupted by oxygen; $C_5$-$C_7$cycloalkylene or —$R_{10}$—O—$R_{12}$—O—$R_{11}$—, when n is 3, $R_1$ is $C_1$-$C_{18}$alkanetriyl or

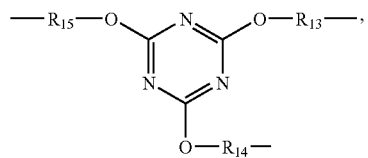

when n is 4, $R_1$ is $C_1$-$C_{18}$alkanetetrayl,

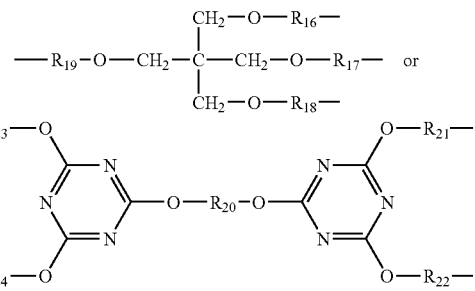

$R_2$, $R_3$ and $R_4$ are each independently of the others $C_1$-$C_{18}$alkyl, $C_2$-$C_{18}$alkenyl, $C_3$-$C_{18}$alkynyl, unsubstituted or $C_1$-$C_4$alkyl-substituted phenyl; $C_7$-$C_9$phenylalkyl, $C_7$-$C_9$phenylalkoxy, $C_1$-$C_{18}$-alkoxy, $C_2$-$C_{18}$alkenyloxy, $C_2$-$C_{18}$alkynyloxy, unsubstituted or $C_1$-$C_4$alkyl-substituted $C_5$-$C_8$-cycloalkyl; unsubstituted or $C_1$-$C_4$alkyl-substituted $C_5$-$C_8$cycloalkoxy;

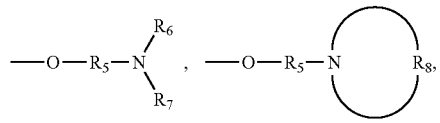

-continued

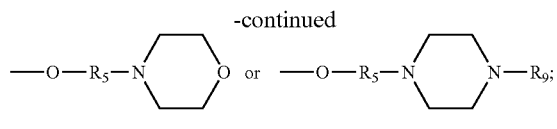 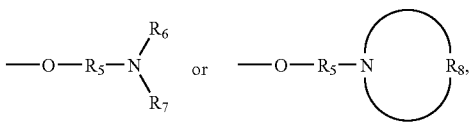

with the proviso that at least one of the radicals $R_2$, $R_3$ or $R_4$ is $C_2$-$C_{18}$alkynyloxy,

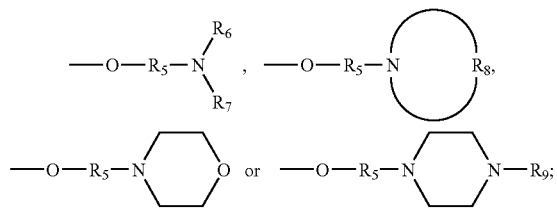

$R_5$ is $C_1$-$C_{12}$alkylene, $C_4$-$C_{12}$alkylene which is interrupted by oxygen; $C_2$-$C_{12}$alkenylene, $C_2$-$C_{12}$alkylidene, $C_7$-$C_{12}$phenylalkylidene, $C_5$-$C_8$cycloalkylene, unsubstituted or $C_1$-$C_4$alkyl-substituted phenylene, $R_6$ and $R_7$ are each independently of one another hydrogen or $C_1$-$C_8$alkyl, $R_8$ is unsubstituted or $C_1$-$C_4$alkyl-substituted $C_2$-$C_8$alkylene;

$R_9$ is $C_1$-$C_{18}$alkyl, $C_4$-$C_{18}$alkyl interrupted by oxygen; $C_7$-$C_9$phenylalkyl, unsubstituted or $C_1$-$C_4$alkyl-substituted $C_5$-$C_8$cycloalkyl; unsubstituted or $C_1$-$C_4$alkyl-substituted phenyl;

$R_{10}$ and $R_{11}$ are each independently of one another $C_1$-$C_{12}$alkylene, $C_4$-$C_{18}$alkylene which is interrupted by oxygen; $C_2$-$C_{18}$alkenylene, $C_2$-$C_{12}$alkylidene, $C_7$-$C_{12}$phenylalkylidene, $C_5$-$C_8$-cycloalkylene, unsubstituted or $C_1$-$C_4$alkyl-substituted phenylene;

$R_{12}$ is $C_1$-$C_{18}$alkylene, $C_4$-$C_{18}$alkylene which is interrupted by oxygen; $C_2$-$C_{18}$alkenylene, $C_2$-$C_{12}$alkylidene, $C_7$-$C_{12}$phenylalkylidene, $C_5$-$C_8$cycloalkylene, unsubstituted or $C_1$-$C_4$alkyl-substituted phenylene; unsubstituted or $C_1$-$C_4$alkyl-substituted naphthylene; or

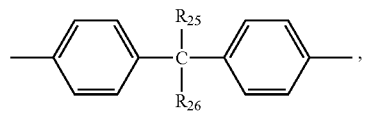

$R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are each independently of the others $C_1$-$C_{18}$alkylene, $C_4$-$C_{18}$alkylene which is interrupted by oxygen; $C_2$-$C_{18}$alkenylene, $C_2$-$C_{12}$alkylidene, $C_7$-$C_{12}$phenylalkylidene, $C_5$-$C_8$cycloalkylene, unsubstituted or $C_1$-$C_4$alkyl-substituted phenylene;

$R_{25}$ and $R_{26}$ are each independently of one another hydrogen, $CF_3$, $C_1$-$C_{12}$alkyl or phenyl, or $R_{25}$ and $R_{26}$ together with the linking carbon atom, form a $C_5$-$C_8$cycloalkylidene ring which is unsubstituted or substituted by 1 to 3 $C_1$-$C_4$alkyl groups; and n is 1, 2, 3 or 4.

Likewise of interest is a composition comprising compounds of formula I wherein n is 1 or 2.

Of special interest is a composition comprising compounds of formula I wherein at least one of the radicals $R_2$, $R_3$ or $R_4$ is $C_3$-$C_4$alkynyloxy, $R_5$ is $C_1$-$C_{12}$alkylene, $C_4$-$C_{12}$alkylene which is interrupted by oxygen; or $C_2$-$C_{12}$alkenylene, $R_6$ and $R_7$ are each independently of one another $C_1$-$C_4$alkyl, and $R_8$ is $C_4$-$C_6$alkylene.

Likewise of special interest is a composition comprising compounds of formula I wherein, when n is 1, $R_1$ is $C_1$-$C_{18}$alkyl, $C_2$-$C_8$alkenyl, $C_3$-$C_8$alkynyl, phenyl; benzyl, $C_1$-$C_{12}$alkoxy, $C_2$-$C_{12}$alkenyloxy, $C_2$-$C_{12}$alkynyloxy, $C_5$-$C_8$cycloalkyl, $C_5$-$C_8$cycloalkoxy,

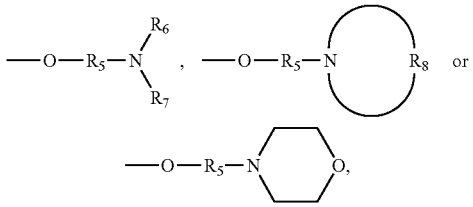

when n is 2, $R_1$ is $C_2$-$C_{18}$alkylene, $C_4$-$C_{18}$alkylene interrupted by oxygen; or —$R_{10}$—O—$R_{12}$—O—$R_{11}$—, when n is 3, $R_1$ is $C_4$-$C_{12}$alkanetriyl or

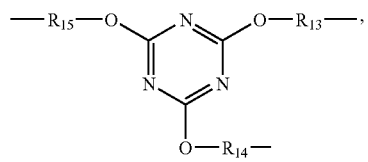

when n is 4, $R_1$ is $C_5$-$C_{12}$alkanetetrayl,

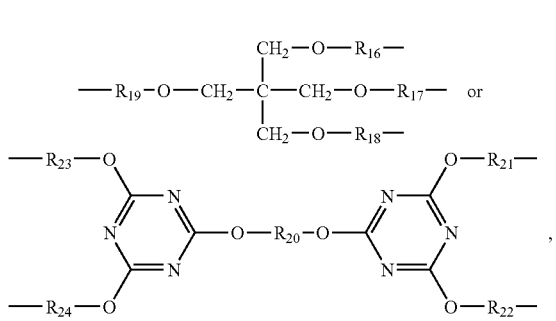

$R_2$, $R_3$ and $R_4$ are each independently of the others $C_1$-$C_8$alkyl, $C_2$-$C_8$alkenyl, $C_3$-$C_8$alkynyl, phenyl; benzyl, phenylethoxy, $C_1$-$C_{12}$alkoxy, $C_3$-$C_{12}$alkenyloxy, $C_3$-$C_{12}$alkynyloxy, $C_5$-$C_8$cycloalkyl, $C_5$-$C_8$cycloalkoxy,

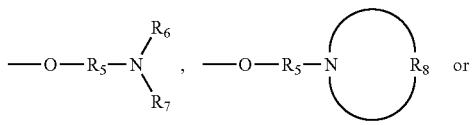

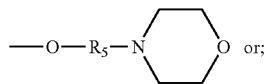

with the proviso that at least one of the radicals $R_2$, $R_3$ or $R_4$ is $C_3$-$C_{12}$alkynyloxy,

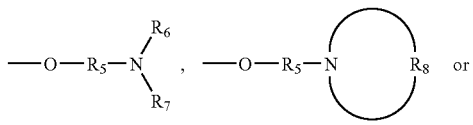

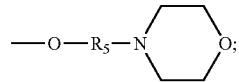

$R_5$ is $C_2$-$C_8$alkylene, $C_4$-$C_8$alkylene which is interrupted by oxygen; $C_4$-$C_8$alkenylene, $C_2$-$C_8$-alkylidene, benzylidene, cyclohexylene or phenylene, $R_6$ and $R_7$ are each independently of one another $C_1$-$C_4$alkyl, $R_8$ is $C_4$-$C_6$alkylene, $R_{10}$ and $R_{11}$ are each independently of one another $C_2$-$C_8$alkylene, $C_4$-$C_{18}$alkylene which is interrupted by oxygen; $C_2$-$C_2$alkenylene, $C_2$-$C_8$alkylidene, benzylidene, cyclohexylene or phenylene, $R_{12}$ is $C_2$-$C_{12}$alkylene, $C_4$-$C_{12}$alkylene which is interrupted by oxygen; $C_2$-$C_{12}$alkenylene, $C_2$-$C_8$alkylidene, benzylidene, cyclohexylene, unsubstituted, phenylene, naphthylene or

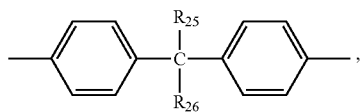

$R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are each independently of the others $C_2$-$C_8$alkylene, $C_4$-$C_8$alkylene which is interrupted by oxygen; $C_4$-$C_6$alkenylene, $C_2$-$C_8$-alkylidene, benzylidene, cyclohexylene or phenylene, $R_{25}$ and $R_{26}$ are each independently of one another hydrogen or $C_1$-$C_4$alkyl, or $R_{25}$ and $R_{26}$ together with the linking carbon atom, form a cyclohexylidene ring; and n is 1, 2, 3 or 4.

Special preference is given to a composition comprising compounds of formula I wherein, when n is 1, $R_1$ is $C_1$-$C_{18}$alkyl, phenyl; benzyl, $C_1$-$C_{12}$alkoxy, $C_3$-$C_6$alkynyloxy,

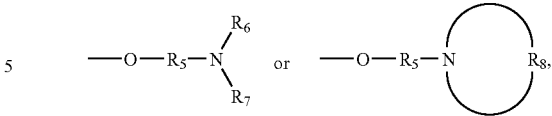

when n is 2,
$R_1$ is $C_4$-$C_{12}$alkylene, $C_4$-$C_{12}$alkylene interrupted by oxygen; or —$R_{10}$—O—$R_{12}$—O—$R_{11}$—,
when n is 3,
$R_1$ is $C_4$-$C_8$alkanetriyl,
when n is 4,
$R_1$ is $C_5$-$C_8$alkanetetrayl,
$R_2$, $R_3$ and $R_4$ are each independently of the others $C_1$-$C_6$alkyl, phenyl; benzyl, phenylethoxy, $C_1$-$C_4$alkoxy, $C_3$-$C_8$alkenyloxy, $C_3$-$C_8$alkynyloxy, cyclohexyl, cyclohexyloxy,

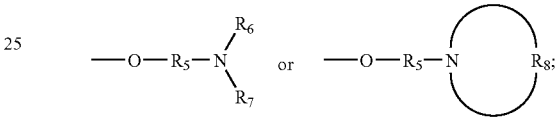

with the proviso that at least one of the radicals $R_2$, $R_3$ or $R_4$ is $C_3$-$C_8$alkynyloxy,

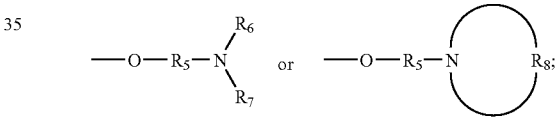

$R_5$ is $C_2$-$C_8$alkylene or $C_4$-$C_8$alkylene which is interrupted by oxygen;

$R_6$ and $R_7$ are each independently of one another $C_1$-$C_4$alkyl, $R_8$ is $C_4$-$C_5$alkylene, $R_{10}$ and $R_{11}$ are each independently of one another $C_2$-$C_8$alkylene or $C_4$-$C_{18}$alkylene which is interrupted by oxygen;

$R_{12}$ is $C_2$-$C_8$alkylene, $C_4$-$C_8$alkylene which is interrupted by oxygen; or

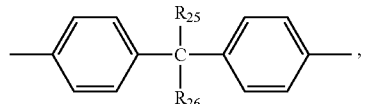

$R_{25}$ and $R_{26}$ are each independently of one another hydrogen or $C_1$-$C_4$alkyl, or $R_{25}$ and $R_{26}$ together with the linking carbon atom, form a cyclohexylidene ring; and n is 1, 2, 3 or 4.

Compositions of very particular interest are those in which component (b) is a compound of the formula I wherein, when n is 1, $R_1$ $C_1$-$C_{12}$alkyl, phenyl or

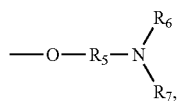

when n is 2, $R_1$ is $C_6$-$C_{10}$alkylene or —$R_{10}$—O—$R_{12}$—O—$R_{11}$—, $R_2$, $R_3$ and $R_4$ are each independently of the others $C_1$-$C_3$alkyl, phenyl; phenylethoxy, $C_3$-$C_4$-alkynyloxy;

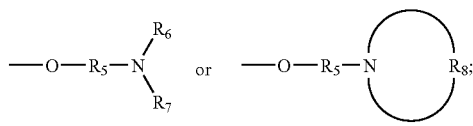

with the proviso that at least one of the radicals $R_2$, $R_3$ or $R_4$ is $C_3$-$C_4$alkynyloxy,

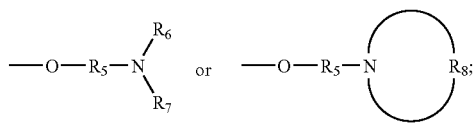

$R_5$ is $C_2$-$C_4$alkylene, $R_6$ and $R_7$ are each independently of one another methyl or ethyl, $R_8$ is $C_4$-$C_5$alkylene, $R_{10}$ and $R_{11}$ are each independently of one another $C_2$-$C_4$alkylene, $R_{12}$ is

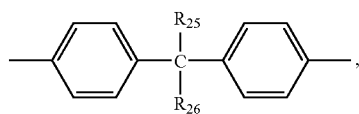

$R_{25}$ and $R_{26}$ are each independently of one another hydrogen or $C_1$-$C_4$alkyl; and n is 1 or 2.

Most of the compounds of the formula I are known or can be prepared in analogy to the process disclosed for example in U.S. Pat. No. 4,406,807.

The compounds of the formula I are suitable as corrosion inhibitors in carriers for protecting metallic surfaces, for example iron, steel, copper, zinc or aluminum, and their alloys.

A preferred carrier is for example a packaging material, an oil, a grease, a wax, a gel, an emulsion, a surface-coating material comprising an organic film-forming binder, an inorganic solid, a paper, a fabric, a natural, semi-synthetic or synthetic polymer.

Preferred organic film-forming binders are epoxy resins, polyurethane resins, polyester resins, acrylic resins and copolymer resins thereof, polyvinyl resins alkyd resins or mixtures of such resins.

Examples for inorganic solids are clays, silica or zeolithes.

Examples of natural, semi-synthetic or synthetic polymers are:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch. Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrile/vinyl halide copolymers or acrylonitrile/ alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene iso-phthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polyketones.

21. Polysulfones, polyether sulfones and polyether ketones.

22. Crosslinked polymers derived from aldehydes on the one hand and phenols, ureas and melamines on the other hand, such as phenol/formaldehyde resins, urea/formaldehyde resins and melamine/formaldehyde resins.

23. Drying and non-drying alkyd resins.

24. Unsaturated polyester resins derived from copolyesters of saturated and unsaturated dicarboxylic acids with polyhydric alcohols and vinyl compounds as crosslinking agents, and also halogen-containing modifications thereof of low flammability.

25. Crosslinkable acrylic resins derived from substituted acrylates, for example epoxy acrylates, urethane acrylates or polyester acrylates.

26. Alkyd resins, polyester resins and acrylate resins crosslinked with melamine resins, urea resins, isocyanates, isocyanurates, polyisocyanates or epoxy resins.

27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

28. Blends of the aforementioned polymers (polyblends), for example PP/EPDM, Poly-amide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Of special interest are compositions comprising as carrier a synthetic polymer, especially a polyolefin, in particular polyethylene, polypropylene or polybutylene or a copolymer thereof with a monoolefin or diolefin.

Also of interest are compositions comprising as carrier biodegradable polymers like for example poly-3-hydroxybutyrate, polysaccharide, polyethylene succinate, polybutylene succinate, polybutylene succinate/adipate, polybutylene succinate/carbonate, polybutylene succinate/terephthalate, polycaprolactone, polylactic acid, polyvinyl alcohol, starch, starch-based PCL, starch-based polyvinyl alcohol, cellulose acetate, or chitosan-cellulose.

The compounds of the formula I are preferably added to the carrier in an amount of from 0.02 to 5%, in particular from 0.10 to 5%, for example from 0.50 to 3%, based on the weight of the carrier.

In addition to components (a) and (b) the novel compositions may comprise further additives (costabilizers) such as, for example, the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl) phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenyl, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis (3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2methylphenol), 4,4'-thiobis(3,6-di-sec-amylphenol), 4,4'-bis(2,6-dimethyl-4-hydroxyphenyl)-disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis [6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl) butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl) propane, 2,2-bis-(5-tert-butyl-4-hydroxy2-methylphenyl)-4-n-dodecylmercaptobutane, 1,1,5,5-tetra(5-tert-butyl-4-hydroxy-2-methylphenyl)pentane.

1.7. O- N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl) sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, didodecylmercaptoethyl-2,2-bis (3,5-di-tert-butyl-4-hydroxybenzyl) malonate, bis[4-(1,1,3,3-tetramethylbutyl) phenyl]-2,2-bis(3,5-di-tert-butyl-4-hydroxybenzyl) malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4, 6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of D-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis (4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino] ethane, 1,2-bis(phenylamino) propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene.

2. UV absorbers and light stabilizers 2.1. 2-(2'-Hydroxyphenyl)benzotriazoles, for example 2-(2'-hydroxy-5'-methylphenyl)benzotriazole, 2-(2'-hydroxy-5'-(1,1,3,3-tetramethylbutyl)phenyl)benzotriazole, 2-(3',5'-di-tert-butyl-2-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl) benzotriazole, 2-(3',5'-di-tert-amyl-2'-hydroxyphenyl) benzotriazole, 2-(3',5'-bis(α,α-dimethylbenzyl)-2'-hydroxyphenyl)benzotriazole, 2-(3'-tert-butyl-2'-hydroxy-5'-2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$, where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl)phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3, 5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5] decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7, 7,9,9-tetramethyl-1,3,8-triazaspiro[4.5]decane-2,4-dione, 3-dodecyl-1-(2,2,6,6-tetramethyl-4-piperidyl)pyrrolidine-2, 5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4, 6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2, 6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4, 6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-(2-hydroxy-4-[3-(2-ethylhexyl-1-oxy)-2-hydroxypropyloxy]phenyl)-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2, 4-di-tert-butylphenyl) phosphite, diisodecyl pentaerythritol diphosphite, bis(2,4-di-tert-butylphenyl)pentaerythritol diphosphite, bis(2,4-dicumylphenyl) pentaerythritol diphosphite, bis(2,6-di-tert-butyl-4-methylphenyl)pentaerythritol diphosphite, diisodecyloxypentaerythritol diphosphite, bis (2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2''-nitrilo[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenylnitrone, N-ethyl-alpha-methyinitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecyinitrone, N-octadecyl-alpha-hexadecylnitrone, nitrone derived from N,N-dialkylhydroxylamine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercapto-benzimidazole, zinc dibutyldithiocarbamate, dioctadecyl disulfide, pentaerythritol tetrakis(β-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene) sorbitol, and 1,3:2,4-di(benzylidene)sorbitol.

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis [5,7-di-tert-butyl-3-(4-[2-hydroxyethoxy]phenyl) benzofuran-2-one], 5,7-di-tert-butyl-3-(4-ethoxyphenyl) benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one.

The additives are added, for example, in concentrations of 0.01 to 10%, relative to the total weight of the carrier.

Preferred further additives are phenolic antioxidants, light-stabilizers and/or processing stabilizers.

Incorporation of the compounds of the formula I and, if desired, further additives into the synthetic polymers is carried out by known methods, for example before or during moulding or else by applying the dissolved or dispersed compounds to the synthetic polymer, if appropriate with subsequent slow evaporation of the solvent. The compounds of the formula I can also be added to the synthetic polymers in the form of a masterbatch containing them, for example, in a concentration of 2.5 to 25% by weight.

The compounds of the formula I can be incorporated into synthetic polymers at high temperature processing condition.

The compounds of the formula I, with or without further additives, can be incorporated in pure form or encapsulated in waxes, oils or polymers into the synthetic polymer.

The compounds of the formula I, with or without further additives, can also be sprayed onto the synthetic polymer. It is able to dilute other additives (for example the conventional additives indicated above) or their melts so that they too can be sprayed together with these additives onto the polymer.

In the case of spherically polymerized polyolefins it may, for example, be advantageous to apply the compounds of the formula I, with or without other additives, by spraying.

The materials treated in this way can be employed in a wide variety of forms, for example as foams, films, fibres, tapes, moulding compositions or as binders for coating materials.

The present invention also relates to new compounds of the formula I

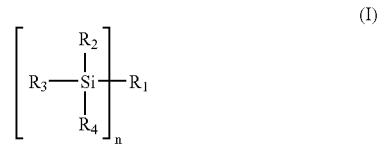

(I)

wherein $R_1$ is $C_1$-$C_{25}$alkyl, $C_2$-$C_{25}$alkenyl, $C_2$-$C_{25}$alkynyl, unsubstituted or $C_1$-$C_4$alkyl-substituted phenyl; $C_7$-$C_9$phenylalkyl, unsubstituted or $C_1$-$C_4$alkyl-substituted $C_5$-$C_8$cycloalkyl;

$R_2$, $R_3$ and $R_4$ are each independently of the others

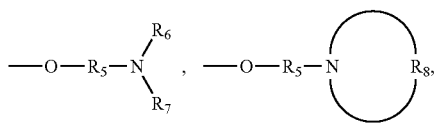

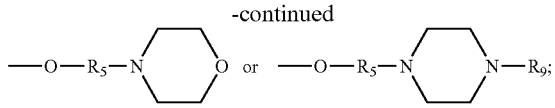

$R_5$ is $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene, $R_6$ and $R_7$ are each independently of one another hydrogen or $C_1$-$C_8$alkyl, $R_8$ is unsubstituted or $C_1$-$C_4$alkyl-substituted $C_2$-$C_{12}$alkylene;

$R_9$ is $C_1$-$C_{25}$alkyl, $C_2$-$C_{25}$alkyl interrupted by oxygen; $C_7$-$C_9$phenylalkyl, unsubstituted or $C_1$-$C_4$alkyl-substituted $C_5$-$C_8$cycloalkyl; unsubstituted or $C_1$-$C_4$alkyl-substituted phenyl; and n is 1.

Of interest are the new compounds of the formula I wherein $R_1$ is $C_1$-$C_{25}$alkyl, $C_2$-$C_{25}$alkenyl, $C_3$-$C_{25}$alkynyl, unsubstituted or $C_1$-$C_4$alkyl-substituted phenyl; $C_7$-$C_9$phenylalkyl, unsubstituted or $C_1$-$C_4$alkyl-substituted $C_5$-$C_8$cycloalkyl.

Of special interest are the new compounds of the formula I wherein $R_1$ is $C_{10}$-$C_{12}$alkyl, $R_2$, $R_3$ and $R_4$ are each independently of the others

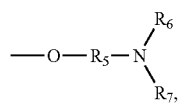

$R_5$ is $C_2$-$C_4$alkylene, $R_6$ and $R_7$ are each independently of one another methyl or ethyl, and n is 1.

The present invention also relates to a method of protecting a corrodible metal substrate, which comprises applying to this substrate a composition comprising a component (a) and (b).

A preferred embodiment of the present invention is therefore the use of a compound of the formula I as corrosion inhibitor in carriers for protecting metallic surfaces.

The following Examples illustrate the invention further. Parts or percentages relate to weight.

EXAMPLE 1

Preparation of Compound 101

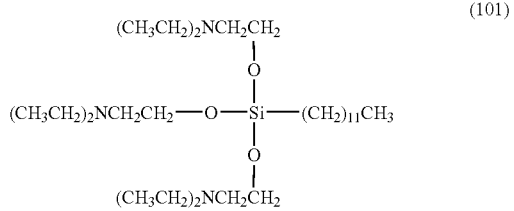

a) Preparation of Trichlorododecylsilane with 1-dodecene and Trichlorosilane.

In a round bottomed flask 60 g of freshly distilled 1-dodecene is treated with 3 ml of a 2% solution of hexachloroplatinic acid [$H_2PtCl_6$] in isopropanol and stirred for 30 minutes at room temperature. The solution is warmed to 40-45° C. and then added 62.7 g (30% excess) of trichlorosilane. The exothermic reaction is maintained at 55-65° C. and stirred for another hour. Distillation under reduced pressure (boiling point 115- 120° C. at 1 mbar) gives 90 g of trichlorododecylsilane, colorless oil.

b) Preparation of Compound (101).

To a solution of 87.5 g of N,N-diethylaminoethanol and 120 ml triethylamine in 250 g of toluene is added 60 g of trichlorododecylsilane [prepared according to Example 1a] controlling the exothermic reaction at the temperature range of 65-70° C. The reaction mixture is maintained at 70° C. for 4 hours. The reaction mixture is cooled to room temperature, filtered and the filtrate concentrated using a vacuum rotary evaporator. Distillation under reduced pressure (boiling point 220° C. at 0.1 mbar) gives 70 g of compound (101), yellow, viscous oil.

EXAMPLE 2

Preparation of Compound (102)

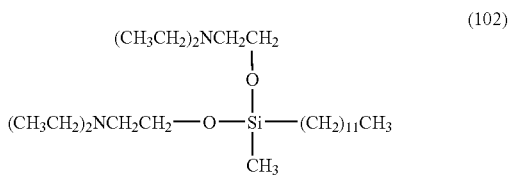

In analogy to Example 1b starting from dichlorododecylmethylsilane [prepared in analogy to Example 1a starting from dichloromethylsilane instead of trichlorosilane] instead of trichlorododecylsilane, compound (102), b.p. 180-185° C. at 0.4 mbar, is obtained.

EXAMPLE 3

Preparation of Compound 103

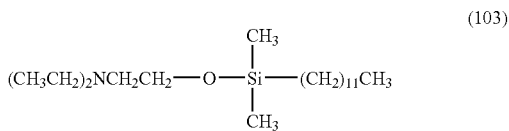

In analogy to Example 1b starting from chlorododecyldimethylsilane [prepared in analogy to Example 1a starting from chlorodimethylsilane instead of trichlorosilane] instead of trichlorododecylsilane, compound (103), colorless oil, is obtained. NMR [300 MHz, CDCl$_3$, δ (ppm)]: 3.61 (t, 2 H); 2.53 (m, 6 H); 1.23 (m, 20 H); 0.98 (t, 6 H); 0.87 (t, 3 H); 0.55 (t, 2 H); 0.073 (s, 6 H).

EXAMPLE 4

Preparation of Compound (104)

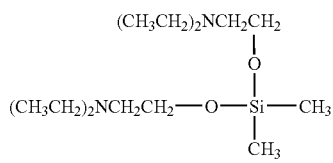

In analogy to Example 1b starting from dichlorodimethylsilane instead of trichlorododecylsilane, compound (104), colorless oil, b.p. 110-113° C. at 3 mbar, is obtained.

EXAMPLE 5

Preparation of Compound (105)

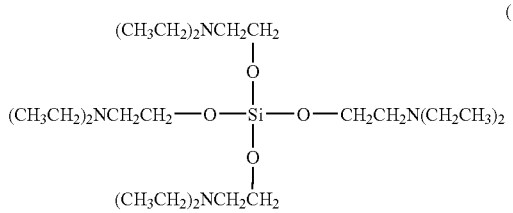

Compound (105) is obtained by transetherification of tetraethoxysilane with N,N-diethylaminoethanol without solvent at 130° C. with dibutyltinoxide as catalyst. B.p. 162-166° C. at 0.3 mbar.

EXAMPLE 6

Preparation of Compound (106)

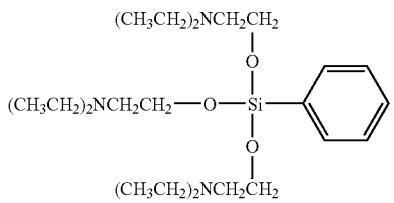

In analogy to Example 1b starting from trichlorophenylsilane instead of trichlorododecylsilane, compound (106), colorless oil, b.p. 190-195° C. at 1 mbar, is obtained.

EXAMPLE 7

Preparation of Compound (107)

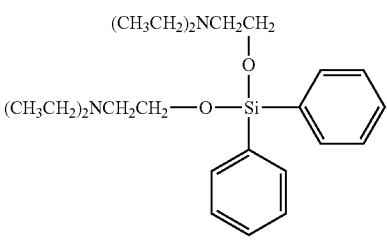

In analogy to Example 1b starting from dichlorodiphenylsilane instead of trichlorododecylsilane, compound (107), yellow oil, b.p. 165-170° C. at 1 mbar, is obtained.

EXAMPLE 8

Preparation of Compound (108)

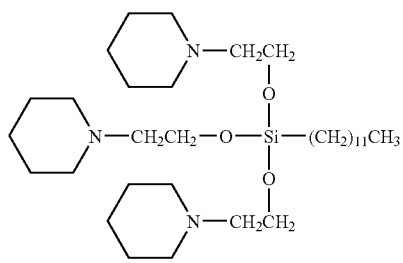

In analogy to Example 1b starting from 2-piperidin-1-yl-ethanol instead of N,N-diethylaminoethanol, compound (108), orange oil, is obtained. NMR [300 MHz, CDCl$_3$, δ (ppm)]: 3.84 (t, 6 H); 2.47 (t, 6 H); 2.39 (t, 12 H); 1.54-1.37 (m, 18 H); 1.21 (m, 20 H); 0.83 (t, 3 H); 0.61 (t, 2 H).

EXAMPLE 9

Preparation of Compound (109)

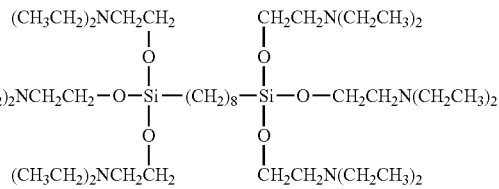

In analogy to Example 1b starting from 1,8-bis(trichlorosilyl)octane [prepared in analogy to Example 1a starting from 1,7-octadiene instead of 1-dodecene] instead of trichlorododecylsilane, compound (109), orange oil, is obtained. NMR [300 MHz, CDCl$_3$, δ (ppm)]: 3.74 (t, 12 H); 2.54 (m, 36 H); 1.21 (m, 12 H); 0.97 (m, 36 H); 0.57 (t, 4 H).

EXAMPLE 10

Preparation of Compound (110)

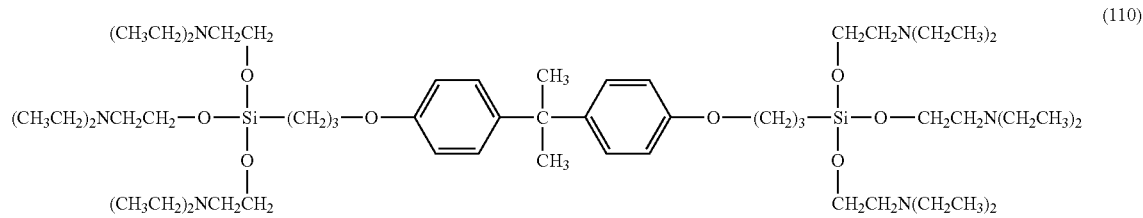

In analogy to Example 1b starting from silane, [(1-methylethylidene)bis(1,4-phenylenoxy-1,3-propanediyl)]bis[trichloro] instead of trichlorododecylsilane, compound (110) is obtained. NMR [300 MHz, CDCl$_3$, δ (ppm)]: 7.06 (dd, 8 H); 3.79 (m, 16 H); 2.55 (m, 36 H); 1.91 (m, 4 H); 1.59 (s, 6 H); 0.99 (t, 36 H); 0.80 (t, 4 H).

EXAMPLE 11

Preparation of Compound (111)

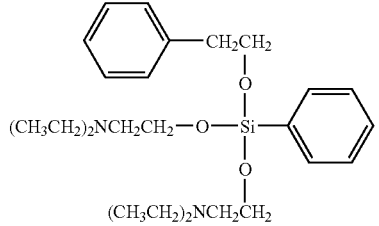

To a solution of 2 mol N,N-diethylaminoethanol, 1 mol 2-phenylethanol and 120 ml triethylamine in 250 g of toluene is added 1 mol of trichlorbphenylsilane controlling the exothermic reaction at the temperature range of 65-70° C. The reaction mixture is maintained at 70° C. for 4 hours. The reaction mixture is cooled to room temperature, filtered and the filtrate concentrated using a vacuum rotary evaporator. Distillation under reduced pressure gives mainly compound (111). NMR [300 MHz, CDCl$_3$, δ (ppm)]: 7.3-7.1 (m, 10 H); 4.0-3.8 (m, 6 H); 2.87 (m, 2 H); 2.6-2.5 (m, 12 H); 0.99 (m, 12 H).

EXAMPLE 12

Preparation of Compound (112)

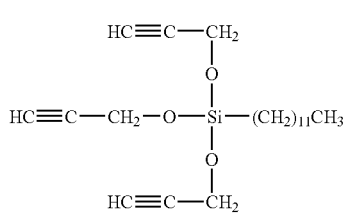

In analogy to Example 1b starting from propargyl alcohol instead of N,N-diethylaminoethanol, compound (112), b.p. 130-135° C. at 1 mbar, is obtained.

EXAMPLE 13

Corrosion Inhibition

The corrosion inhibiting ability of the products is assessed according to the FED.TEST METHOD STD. NO. 101C procedure A: Ten milliliters of glycerin-water solution having a specific gravity of about 1.074 at ambient temperature to affect an atmosphere of about 85 percent relative humidity is introduced into the bottom of the test assembly. 0.05±0.005 g of the compounds of the instant invention is introduced in the test assembly in a small vessel placed on the bottom of the jar. The lid is closed tightly. The test assembly is exposed for 20 hours at 24° C. Then, cold water at 0° C. is added to the aluminum tube until full. After 3 hours, the water is removed from the tube and the steel specimen is evaluated for any evidences of corrosion. This test is carried out on 3 test pieces for 8 cycles and on a blank test at the same time. A visual corrosion evaluation is assessed according to the following rating: "none" means no corrosion; "very low" means very low corrosion; "low" means low corrosion; and "high" means high corrosion. The results are summarized in Table 1.

TABLE 1

| | | Visual corrosion | | |
|---|---|---|---|---|
| Example | Corrosion inhibitor | Piece 1 | Piece 2 | Piece 3 |
| 13a[a] | Blank (1 cycle) | high | high | high |
| 13b[b] | Compound 101 (8 cycles) | none | none | none |
| 13c[b] | Compound 102 (8 cycles) | none | none | none |
| 13d[b] | Compound 103 (8 cycles) | none | none | none |
| 13e[b] | Compound 104 (8 cycles) | none | none | none |
| 13f[b] | Compound 106 (8 cycles) | none | none | none |
| 13g[b] | Compound 107 (8 cycles) | none | none | none |
| 13h[b] | Compound 108 (8 cycles) | none | none | none |
| 13i[b] | Compound 109 (8 cycles) | none | none | none |
| 13j[b] | Compound 110 (8 cycles) | none | none | none |
| 13k[b] | Compound 111 (8 cycles) | none | none | none |

[a] Comparison example.
[b] Example according to the invention.

EXAMPLE 14

Corrosion Inhibition with a Polyethylene Powder Carrier 20 g of the compounds of the instant invention is mixed in a turbo mixer with 1000 g of a low density polyethylene [Riblene FF29 (RTM) powder (Polimeri Europa)] having a melt index of 0.6 g/10 min. (measured at 190° C. and 2.16 kg). The mixture is extruded at a maximum temperature of 170° C. using an O.M.C. extruder, to give polymer granules which are subsequently grinded to obtain a powder. 2.5 g of this powder is placed into the vessel of the test assembly and its corrosion inhibiting ability is assessed according to the afore mentioned FED.TEST METHOD STD. NO. 101C procedure A according to Example 13 (with 2.5 g of the powder instead of 0.05 g). The test is carried out on 3 test pieces for 8 cycles and on a blank test at the same time. The results obtained are summarized in Table 2 and compared to a blank test after 1 cycle.

TABLE 2

| | | Visual corrosion | | |
|---|---|---|---|---|
| Example | Corrosion inhibitor | Piece 1 | Piece 2 | Piece 3 |
| 14a[a] | Blank (1 cycle) | high | high | high |
| 14b[b] | 2% compound 107 (8 cycles) | none | none | none |

[a] Comparison example.
[b] Example according to the invention.

EXAMPLE 15

Corrosion Inhibition with a Polyethylene Film Carrier 20 g of the compounds of the instant invention is mixed in a turbo mixer with 1000 g of a low density polyethylene [Riblene FF29 (RTM) powder (Polimeri Europa)] having a melt index of 0.6 g/10 min. (measured at 190° C. and 2.16 kg). The mixture is extruded at a maximum temperature of 170° C. using an O.M.C. extruder, to give polymer granules which are subsequently converted to a film of 100 μm thickness, using a blow-extruder (Formac) and working at a maximum temperature of 210° C. Part of this film is grinded to obtain a powder. 2.5 g of this powder is placed into the vessel of the test assembly and its corrosion inhibiting ability is assessed according to the afore mentioned FED.TEST METHOD STD. NO. 101C procedure A according to Example 13 (with 2.5 g of the powder instead of 0.05 g). The test is carried out on 3 test pieces for 8 cycles and on a blank test at the same time. The results obtained are summarized in Table 3 and compared to a blank test after 1 cycle.

TABLE 3

| | | Visual corrosion | | |
|---|---|---|---|---|
| Example | Corrosion inhibitor | Piece 1 | Piece 2 | Piece 3 |
| 15a[a] | Blank (1 cycle) | high | high | High |
| 15b[b] | 2% compound 101 (8 cycles) | none | none | None |

[a] Comparison example.
[b] Example according to the invention.

Additionally, the corrosion inhibiting ability of the obtained film is assessed according to the FED.TEST METHOD STD. NO. 101C procedure B: Ten milliliters of glycerin-water solution having a specific gravity of about 1.074 at ambient temperature to affect an atmosphere of about 85 percent relative humidity is introduced into the bottom of the test assembly. Two specimens are placed through the parallel slots of the test assembly jar. To fasten the film in position, a part of the specimen is bent onto the outer surface of the lid and this tab and the slot covered with tape having a low water vapor transmission rate. The lid is closed tightly. The test assembly is exposed for 20 hours at 24° C. Then, cold water at 0° C. is added to the aluminum tube until full: After 3 hours, the water is removed from the tube and the steel specimen is evaluated for any evidences of corrosion. This test is carried out on 3 test pieces and on a blank test at the same time. A visual corrosion evaluation is assessed according to the rating used in procedure A. The results are summarized in Table 4.

TABLE 4

| | | Visual corrosion | | |
|---|---|---|---|---|
| Example | Corrosion inhibitor | Piece 1 | Piece 2 | Piece 3 |
| 15c[a] | Blank (1 cycle) | high | high | High |
| 15d[b] | 2% compound 101 (1 cycle) | low | low | low |

[a] Comparison example.
[b] Example according to the invention.

What is claimed is:
1. A composition comprising
   a) as carrier a synthetic polyolefin polymer, and incorporated into the synthetic polymer
   b) as corrosion inhibitor at least one compound of the formula I

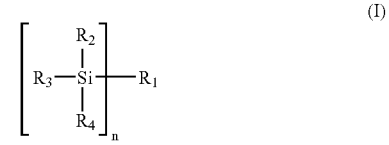

wherein, when n is 1,
$R_1$ is hydrogen, $C_1$-$C_{32}$alkyl, $C_2$-$C_{32}$alkenyl, $C_2$-$C_{32}$alkynyl, unsubstituted or $C_1$-$C_4$alkyl-substituted phenyl; $C_7$-$C_9$phenylalkyl, $C_1$-$C_{32}$alkoxy, $C_2$-$C_{32}$alkenyloxy, $C_2$-$C_{32}$alkynyloxy, unsubstituted or $C_1$-$C_4$alkyl-substituted $C_5$-$C_8$cycloalkyl; unsubstituted or $C_1$-$C_4$alkyl-substituted $C_5$-$C_8$cycloalkoxy

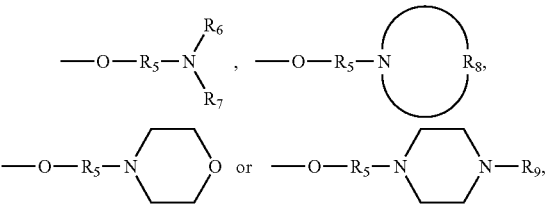

when n is 2,
$R_1$ is $C_1$-$C_{32}$alkylene, $C_2$-$C_{32}$alkylene interrupted by oxygen; $C_5$-$C_8$cycloalkylene or —$R_{10}$—O—$R_{12}$—O—$R_{11}$—,
when n is 3,
$R_1$ is $C_1$-$C_{32}$alkanetriyl,

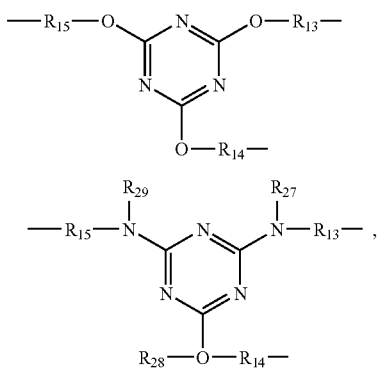

or

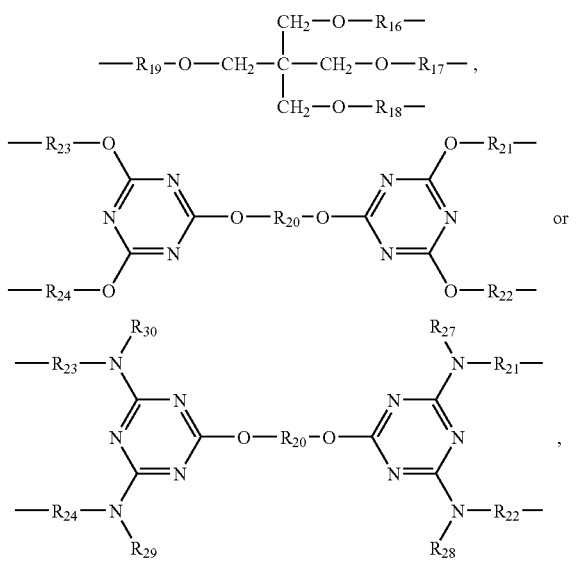

when n is 4, $R_1$ is $C_1$-$C_{32}$alkanetetrayl, $R_2$, $R_3$ and $R_4$ are each independently of the others $C_1$-$C_{32}$alkyl, $C_2$-$C_{32}$alkenyl, $C_2$-$C_{32}$alkynyl, unsubstituted or $C_1$-$C_4$alkyl-substituted phenyl; $C_7$-$C_9$phenylalkyl, $C_7$-$C_9$phenylalkoxy, $C_1$-$C_{32}$alkoxy, $C_2$-$C_{32}$alkenyloxy, $C_2$-$C_{32}$alkynyloxy, unsubstituted or $C_1$-$C_4$alkyl-substituted $C_5$-$C_8$cycloalkyl; unsubstituted or $C_1$-$C_4$alkyl-substituted $C_5$-$C_8$cycloalkoxy;

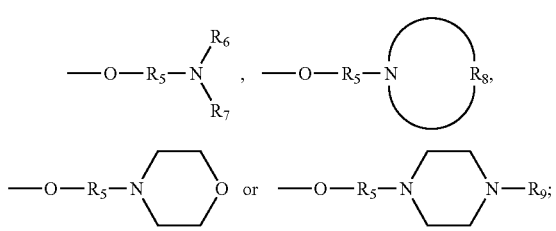

with the proviso that at least one of the radicals $R_2$, $R_3$ or $R_4$ is $C_2$-$C_{32}$alkynyloxy,

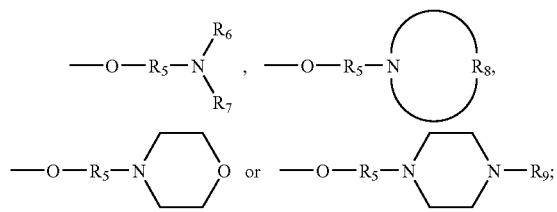

$R_5$ is $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene, $R_6$ and $R_7$ are each independently of one another hydrogen or $C_1$-$C_{12}$alkyl, $R_8$ is unsubstituted or $C_1$-$C_4$alkyl-substituted $C_2$-$C_{12}$alkylene;

$R_9$ is $C_1$-$C_{25}$alkyl, $C_2$-$C_{25}$alkyl interrupted by oxygen; $C_7$-$C_9$phenylalkyl, unsubstituted or $C_1$-$C_4$alkyl-substituted $C_5$-$C_8$cycloalkyl; unsubstituted or $C_1$-$C_4$alkyl-substituted phenyl;

$R_{10}$ and $R_{11}$ are each independently of one another $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene;

$R_{12}$ is $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene; unsubstituted or $C_1$-$C_4$alkyl-substituted naphthylene; or

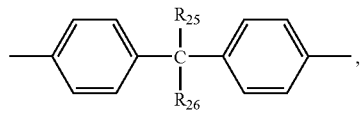

$R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are each independently of the others $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene;

$R_{25}$ and $R_{26}$ are each independently of one another hydrogen, $CF_3$, $C_1$-$C_{12}$alkyl or phenyl, or $R_{25}$ and $R_{26}$ together with the linking carbon atom, form a $C_5$-$C_8$cycloalkylidene ring which is unsubstituted or substituted by 1 to 3 $C_1$-$C_4$alkyl groups;

$R_{27}$, $R_{28}$, $R_{29}$ and $R_{30}$ are each independently of the others hydrogen or $C_1$-$C_8$alkyl; and n is 1, 2, 3 or 4.

2. A composition according to claim 1, wherein, when n is 1, $R_1$ is hydrogen, $C_1$-$C_{32}$alkyl, $C_2$-$C_{32}$alkenyl, $C_3$-$C_{32}$alkynyl, unsubstituted or $C_1$-$C_4$alkyl-substituted phenyl; $C_7$-$C_9$phenylalkyl, $C_1$-$C_{32}$alkoxy, $C_2$-$C_{32}$alkenyloxy, $C_2$-$C_{32}$alkynyloxy, unsubstituted or $C_1$-$C_4$alkyl-substituted $C_5$-$C_8$cycloalkyl; unsubstituted or $C_1$-$C_4$alkyl-substituted $C_5$-$C_8$cycloalkoxy;

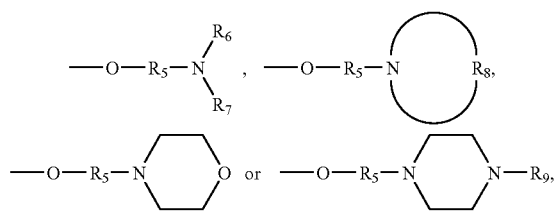

when n is 2, $R_1$ is $C_1$-$C_{32}$alkylene, $C_2$-$C_{18}$alkylene interrupted by oxygen; $C_5$-$C_8$cycloalkylene or —$R_{10}$—O—$R_{12}$—O—$R_{11}$—, when n is 3, $R_1$ is $C_1$-$C_{32}$alkanetriyl,

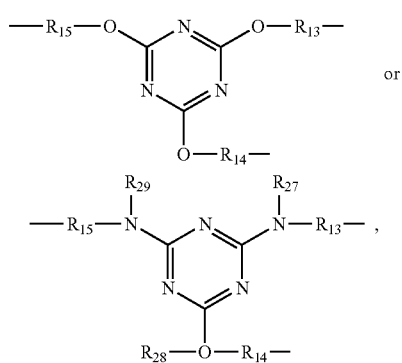

or when n is 4, $R_1$ is $C_1$-$C_{32}$alkanetetrayl,

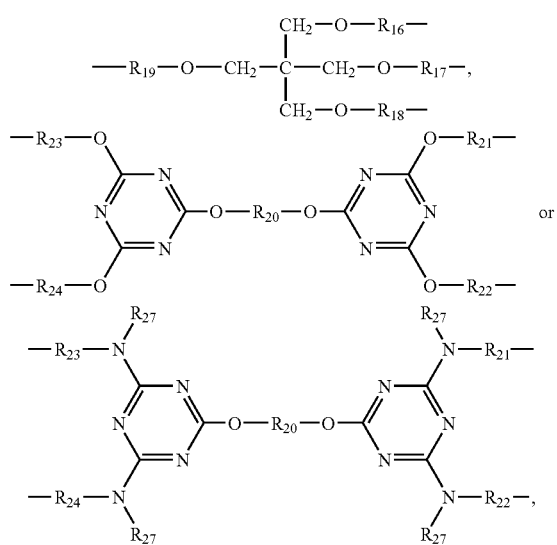

$R_2$, $R_3$ and $R_4$ are each independently of the others $C_1$-$C_{32}$alkyl, $C_2$-$C_{32}$alkenyl, $C_3$-$C_{32}$alkynyl, unsubstituted or $C_1$-$C_4$alkyl-substituted phenyl; $C_7$-$C_9$phenylalkyl, $C_7$-$C_9$phenylalkoxy, $C_1$-$C_{32}$-alkoxy, $C_2$-$C_{32}$alkenyloxy, $C_2$-$C_{32}$alkynyloxy, unsubstituted or $C_1$,-$C_4$alkyl-substituted $C_5$-$C_8$cycloalkyl;

unsubstituted or $C_1$-$C_4$alkyl-substituted $C_5$-$C_8$cycloalkoxy;

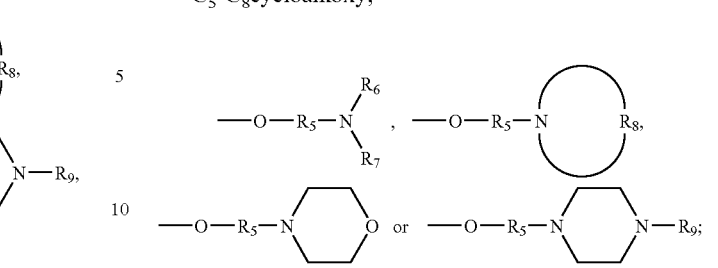

with the proviso that at least one of the radicals $R_2$, $R_3$ or $R_4$ is $C_2$-$C_{32}$alkynyloxy

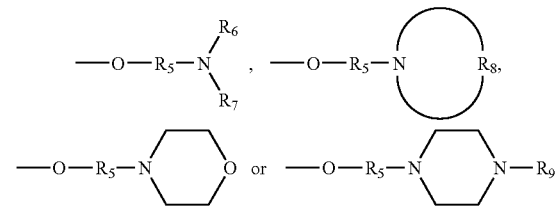

$R_5$ is $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene, $R_6$ and $R_7$ are each independently of one another hydrogen or $C_1$-$C_{12}$alkyl, $R_8$ is unsubstituted or $C_1$-$C_4$alkyl-substituted $C_2$-$C_{12}$alkylene;

$R_9$ is $C_1$-$C_{25}$alkyl, $C_2$-$C_{25}$alkyl interrupted by oxygen; $C_7$-$C_9$phenylalkyl, unsubstituted or $C_1$-$C_4$alkyl-substituted $C_5$-$C_8$cycloalkyl; unsubstituted or $C_1$-$C_4$alkyl-substituted phenyl;

$R_{10}$ and $R_{11}$ are each independently of one another $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$-cycloalkylene, unsubstituted or $C_1$-$C_4$alkyl-substituted phenylene;

$R_{12}$ is $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene; unsubstituted or $C_1$-$C_4$alkyl-substituted naphthylene; or

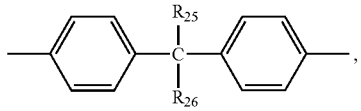

$R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are each independently of the others $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene;

$R_{25}$ and $R_{26}$ are each independently of one another hydrogen, $CF_3$, $C_1$-$C_{12}$alkyl or phenyl, or $R_{25}$ and $R_{26}$ together with the linking carbon atom, form a $C_5$-$C_8$cycloalkylidene ring which is unsubstituted or substituted by 1 to 3 $C_1$-$C_4$alkyl groups;

$R_{27}$ is hydrogen or $C_1$-$C_8$alkyl; and n is 1, 2, 3 or 4.

3. A composition according to claim 1, wherein, when n is 1, $R_1$ is hydrogen, $C_1$-$C_{18}$alkyl, $C_2$-$C_{18}$alkenyl, $C_3$-$C_{18}$alkynyl, unsubstituted or $C_1$-$C_4$alkyl-substituted phenyl; $C_7$-$C_9$phenylalkyl, $C_1$-$C_{18}$alkoxy, $C_2$-$C_{18}$alkenyloxy, $C_2$-$C_{18}$alkynyloxy, unsubstituted or $C_1$-$C_4$alkyl-substituted $C_5$-$C_8$cycloalkyl; unsubstituted or $C_1$-$C_4$alkyl-substituted $C_5$-$C_8$cycloalkoxy;

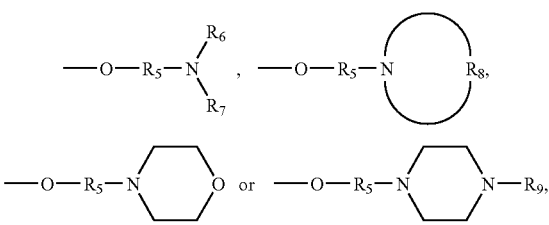

when n is 2, $R_1$ is $C_1$-$C_{18}$alkylene, $C_4$-$C_{18}$alkylene interrupted by oxygen; $C_5$-$C_7$cycloalkylene or —$R_{10}$—O—$R_{12}$—O—$R_{11}$—, when n is 3, $R_1$ is $C_1$-$C_{18}$alkanetriyl or

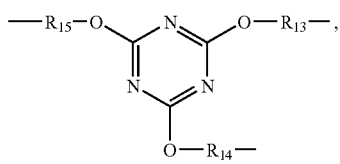

when n is 4, $R_1$ is $C_1$-$C_{18}$alkanetetrayl,

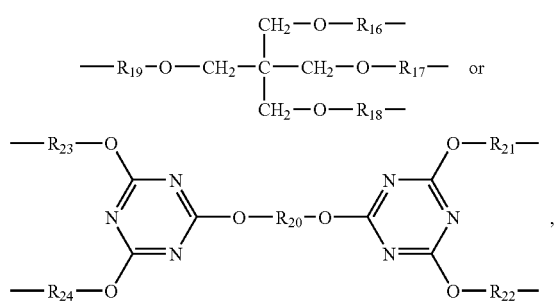

$R_2$, $R_3$ and $R_4$ are each independently of the others $C_1$-$C_{18}$alkyl, $C_2$-$C_{18}$alkenyl, $C_3$-$C_{18}$alkynyl, unsubstituted or $C_1$-$C_4$alkyl-substituted phenyl; $C_7$-$C_9$phenylalkyl, $C_7$-$C_9$phenylalkoxy, $C_1$-$C_{18}$alkoxy, $C_2$-$C_{18}$alkenyloxy, $C_2$-$C_{18}$alkynyloxy, unsubstituted or $C_1$-$C_4$alkyl-substituted $C_5$-$C_8$cycloalkyl; unsubstituted or $C_1$-$C_4$alkyl-substituted $C_5$-$C_8$cycloalkoxy;

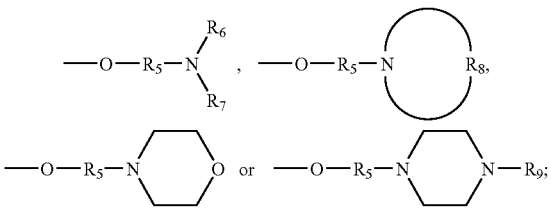

with the proviso that at least one of the radicals $R_2$, $R_3$ or $R_4$ is $C_2$-$C_{18}$alkynyloxy,

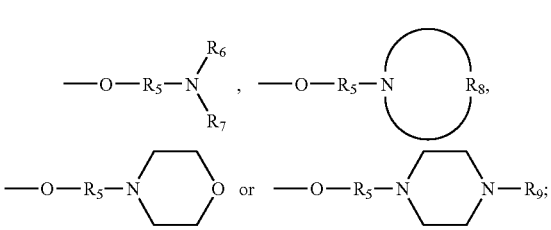

$R_5$ is $C_1$-$C_{12}$alkylene, $C_4$-$C_{12}$alkylene which is interrupted by oxygen; $C_2$-$C_{12}$alkenylene, $C_2$-$C_{12}$alkylidene, $C_7$-$C_{12}$phenylalkylidene, $C_5$-$C_8$cycloalkylene, unsubstituted or $C_1$-$C_4$alkyl-substituted phenylene, $R_6$ and $R_7$ are each independently of one another hydrogen or $C_1$-$C_8$alkyl, $R_8$ is unsubstituted or $C_1$-$C_4$alkyl-substituted $C_2$-$C_8$alkylene;

$R_9$ is $C_1$-$C_{18}$alkyl, $C_4$-$C_{18}$alkyl interrupted by oxygen; $C_7$-$C_9$phenylalkyl, unsubstituted or $C_1$-$C_4$alkyl-substituted $C_5$-$C_8$cycloalkyl; unsubstituted or $C_1$-$C_4$alkyl-substituted phenyl;

$R_{10}$ and $R_{11}$ are each independently of one another $C_1$-$C_{12}$alkylene, $C_4$-$C_{18}$alkylene which is interrupted by oxygen; $C_2$-$C_{18}$alkenylene, $C_2$-$C_{12}$alkylidene, $C_7$-$C_{12}$phenylalkylidene, $C_5$-$C_8$cycloalkylene, unsubstituted or $C_1$-$C_4$alkyl-substituted phenylene;

$R_{12}$ is $C_1$-$C_{18}$alkylene, $C_4$-$C_{18}$alkylene which is interrupted by oxygen; $C_2$-$C_{18}$alkenylene, $C_2$-$C_{12}$alkylidene, $C_7$-$C_{12}$phenylalkylidene, $C_5$-$C_8$cycloalkylene, unsubstituted or $C_1$-$C_4$alkyl-substituted phenylene; unsubstituted or $C_1$-$C_4$alkyl-substituted naphthylene; or

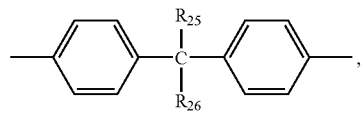

$R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are each independently of the others $C_1$-$C_{18}$alkylene, $C_4$-$C_{18}$alkylene which is interrupted by oxygen; $C_2$-$C_{18}$alkenylene, $C_2$-$C_{12}$alkylidene, $C_7$-$C_{12}$phenylalkylidene, $C_5$-$C_8$cycloalkylene, unsubstituted or $C_1$-$C_4$alkyl-substituted phenylene;

$R_{25}$ and $R_{26}$ are each independently of one another hydrogen, $CF_3$, $C_1$-$C_{12}$alkyl or phenyl, or $R_{25}$ and $R_{26}$ together with the linking carbon atom, form a $C_5$-$C_8$cycloalkylidene ring which is unsubstituted or substituted by 1 to 3 $C_1$-$C_4$alkyl groups; and n is 1, 2, 3 or 4.

4. A composition according to claim 1, wherein n is 1 or 2.

5. A composition according to claim 1, wherein at least one of the radicals $R_2$, $R_3$ or $R_4$ is $C_3$-$C_4$alkynyloxy,

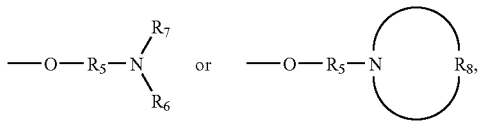

$R_5$ is $C_1$-$C_{12}$alkylene, $C_4$-$C_{12}$alkylene which is interrupted by oxygen; or $C_2$-$C_{12}$alkenylene, $R_6$ and $R_7$ are each independently of one another $C_1$-$C_4$alkyl, and $R_8$ is $C_4$-$C_6$alkylene.

6. A composition according to claim 1, wherein, when n is 1, $R_1$ is $C_1$-$C_{18}$alkyl, $C_2$-$C_8$alkenyl, $C_3$-$C_8$alkynyl, phenyl; benzyl, $C_1$-$C_{12}$alkoxy, $C_2$-$C_{12}$alkenyloxy, $C_2$-$C_{12}$alkynyloxy, $C_5$-$C_8$cycloalkyl, $C_5$-$C_8$cycloalkoxy,

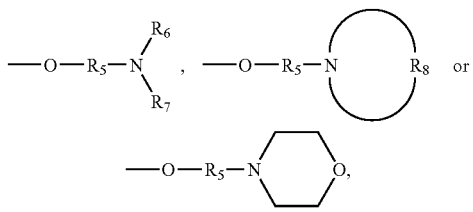

when n is 2, $R_1$ is $C_2$-$C_{18}$alkylene, $C_4$-$C_{18}$alkylene interrupted by oxygen; or —$R_{10}$—O—$R_{12}$—O—$R_{11}$—, when n is 3, $R_1$ is $C_4$-$C_{12}$alkanetriyl or

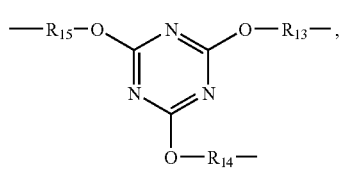

when n is 4, $R_1$ is $C_5$-$C_{12}$alkanetetrayl,

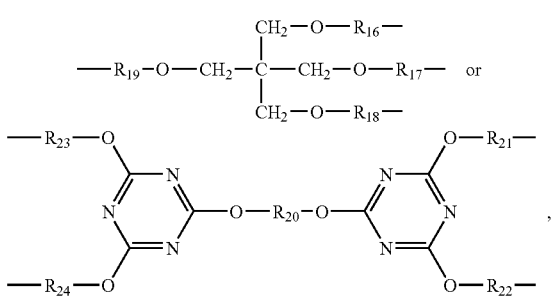

$R_2$, $R_3$ and $R_4$ are each independently of the others $C_1$-$C_8$alkyl, $C_2$-$C_8$alkenyl, $C_3$-$C_8$alkynyl, phenyl; benzyl, phenylethoxy, $C_1$-$C_{12}$alkoxy, $C_3$-$C_{12}$alkenyloxy, $C_3$-$C_{12}$alkynyloxy, $C_5$-$C_8$cycloalkyl, $C_5$-$C_8$cycloalkoxy,

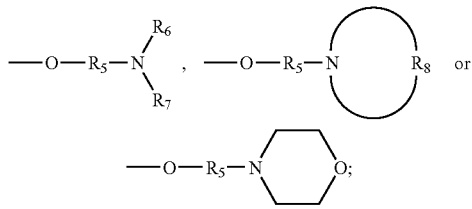

with the proviso that at least one of the radicals $R_2$, $R_3$ or $R_4$ is $C_3$-$C_{12}$alkynyloxy,

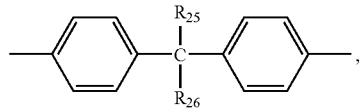

$R_5$ is $C_2$-$C_8$alkylene, $C_4$-$C_8$alkylene which is interrupted by oxygen; $C_4$-$C_8$alkenylene, $C_2$-$C_8$alkylidene, benzylidene, cyclohexylene or phenylene, $R_6$ and $R_7$ are each independently of one another $C_1$-$C_4$alkyl, $R_8$ is $C_4$-$C_6$alkylene, $R_{10}$ and $R_{11}$ are each independently of one another $C_2$-$C_8$alkylene, $C_4$-$C_{18}$alkylene which is interrupted by oxygen; $C_2$-$C_2$alkenylene, $C_2$-$C_8$alkylidene, benzylidene, cyclohexylene or phenylene, $R_{12}$ is $C_2$-$C_{12}$alkylene, $C_4$-$C_{12}$alkylene which is interrupted by oxygen; $C_2$-$C_{12}$alkenylene, $C_2$-$C_8$alkylidene, benzylidene, cyclohexylene, unsubstituted, phenylene, naphthylene or $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are each independently of the others $C_2$-$C_8$alkylene, $C_4$-$C_8$alkylene which is interrupted by oxygen; $C_4$-$C_8$alkenylene, $C_2$-$C_8$alkylidene, benzylidene, cyclohexylene or phenylene, $R_{25}$ and $R_{26}$ are each independently of one another hydrogen or $C_1$-$C_4$alkyl, or $R_{25}$ and $R_{26}$ together with the linking carbon atom, form a cyclohexylidene ring; and n is 1, 2, 3 or 4.

7. A composition according to claim 1, wherein, when n is 1, $R_1$ is $C_1$-$C_{18}$alkyl, phenyl; benzyl, $C_1$-$C_{12}$alkoxy, $C_3$-$C_6$alkynyloxy,

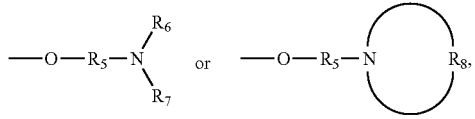

when n is 2, $R_1$ is $C_4$-$C_{12}$alkylene, $C_4$-$C_{12}$alkylene interrupted by oxygen; or —$R_{10}$—O—$R_{12}$—O—$R_{11}$—, when n is 3, $R_1$ is $C_4$-$C_8$alkanetriyl, when n is 4, $R_1$ is $C_5$-$C_8$alkanetetrayl, $R_2$, $R_3$ and $R_4$ are each independently of the others $C_1$-$C_6$alkyl, phenyl; benzyl, phenylethoxy, $C_1$-$C_4$alkoxy, $C_3$-$C_8$alkenyloxy, $C_3$-$C_8$alkynyloxy, cyclohexyl, cyclohexyloxy,

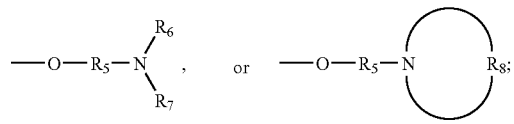

with the proviso that at least one of the radicals $R_2$, $R_3$ or $R_4$ is $C_3$-$C_8$alkynyloxy,

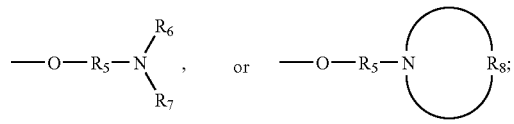

$R_5$ is $C_2$-$C_8$alkylene or $C_4$-$C_8$alkylene which is interrupted by oxygen;

$R_6$ and $R_7$ are each independently of one another $C_1$-$C_4$alkyl, $R_8$ is $C_4$-$C_5$alkylene, $R_{10}$ and $R_{11}$ are each independently of one another $C_2$-$C_8$alkylene or $C_4$-$C_{18}$alkylene which is interrupted by oxygen;

$R_{12}$ is $C_2$-$C_8$alkylene, $C_4$-$C_8$alkylene which is interrupted by oxygen; or

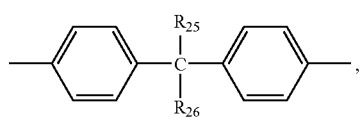

$R_{25}$ and $R_{26}$ are each independently of one another hydrogen or $C_1$-$C_4$alkyl, or $R_{25}$ and $R_{26}$ together with the linking carbon atom, form a cyclohexylidene ring; and n is 1,2, 3or 4.

8. A composition according to claim 1, wherein, when n is 1, $R_1$ $C_1$-$C_{12}$alkyl, phenyl or

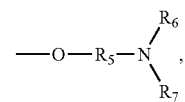

when n is 2, $R_1$ is $C_6$-$C_{10}$alkylene or —$R_{10}$—O—$R_{12}$—O—$R_{11}$—, $R_2$, $R_3$ and $R_4$ are each independently of the others $C_1$-$C_3$alkyl, phenyl; phenylethoxy, $C_3$-$C_4$alkynyloxy;

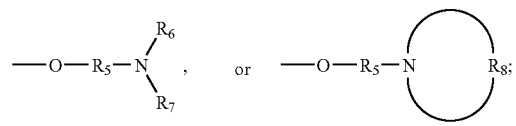

with the proviso that at least one of the radicals $R_2$, $R_3$ or $R_4$ is $C_3$-$C_4$alkynyloxy,

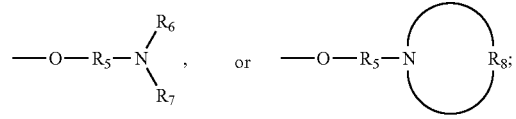

$R_5$ is $C_2$-$C_4$alkylene, $R_6$ and $R_7$ are each independently of one another methyl or ethyl, $R_8$ is $C_4$-$C_5$alkylene, $R_{10}$ and $R_{11}$ are each independently of one another $C_2$-$C_4$alkylene, $R_{12}$ is

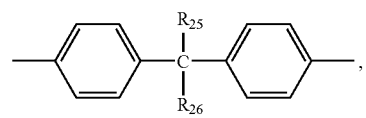

$R_{25}$ and $R_{26}$ are each independently of one another hydrogen or $C_1$-$C_4$alkyl; and n is 1 or 2.

9. A composition according to claim 1, wherein component (a) is a packaging material.

10. A composition according to claim 1, wherein component (a) is polyethylene, polypropy-lene or polybutylene or a copolymer thereof with a monoolefin or diolefin.

11. A composition according to claim 1, wherein component (b) is present in an amount of 0.02 to 5 %, based on the weight of component (a).

12. A composition according to claim 1, comprising in addition to components (a) and (b), further additives.

13. A composition according to claim 12, wherein the further additives are phenolic antioxidants, light-stabilizers or processing stabilizers.

14. A compound of the formula I

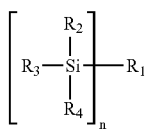

wherein
R₁ is $C_1$-$C_{25}$alkyl, $C_2$-$C_{25}$alkenyl, $C_2$-$C_{25}$alkynyl, unsubstituted or $C_1$-$C_4$alkyl-substituted phenyl; $C_7$-$C_9$phenylalkyl, unsubstituted or $C_1$-$C_4$alkyl-substituted $C_5$-$C_8$cycloalkyl;

$R_2$, $R_3$ and $R_4$ are each independently of the others

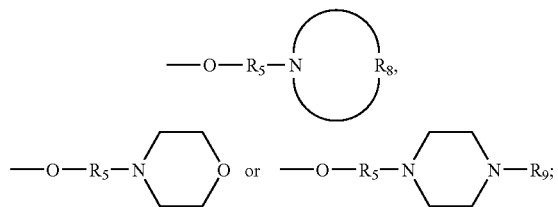

$R_5$ is $C_1$-$C_{18}$alkylene, $C_2$-$C_{18}$alkylene which is interrupted by oxygen; $C_2$-$C_{18}$alkenylene, $C_2$-$C_{20}$alkylidene, $C_7$-$C_{20}$phenylalkylidene, $C_5$-$C_8$cycloalkylene, unsubstituted or $C_1$-$C_4$alkyl-substituted phenylene, $R_6$ and $R_7$ are each independently of one another hydrogen or $C_1$-$C_8$alkyl, $R_8$ is unsubstituted or $C_1$-$C_4$alkyl-substituted $C_2$-$C_{12}$alkylene;

$R_9$ is $C_1$-$C_{25}$alkyl, $C_2$-$C_{25}$alkyl interrupted by oxygen; $C_7$-$C_9$phenylalkyl, unsubstituted or $C_1$-$C_4$alkyl-substituted $C_5$-$C_8$cycloalkyl; unsubstituted or $C_1$-$C_4$alkyl-substituted phenyl; and n is 1.

15. A compound according to claim 14, wherein
R₁ is $C_1$-$C_{25}$alkyl, $C_2$-$C_{25}$alkenyl, $C_3$-$C_{25}$alkynyl, unsubstituted or $C_1$-$C_4$alkyl-substituted phenyl; $C_7$-$C_9$phenylalkyl or unsubstituted or $C_1$-$C_4$alkyl-substituted $C_5$-$C_8$cycloalkyl.

16. A method of protecting a corrodible metal substrate, which comprises applying to this substrate a composition according to claim 1.

* * * * *